(12) United States Patent
Vergnault et al.

(10) Patent No.: US 7,927,624 B2
(45) Date of Patent: Apr. 19, 2011

(54) HYDROPHILIC/LIPOPHILIC POLYMERIC MATRIX DOSAGE FORMULATION

(75) Inventors: Guy Vergnault, Loechle (FR); Pascal Grenier, Kappelen (FR); Lauretta Maggi, Pavia (IT); Ubaldo Conte, Busto Arsizio (IT)

(73) Assignee: Jagotec AG, Muttenz (CH)

( * ) Notice: Subject to any disclaimer, the term of this patent is extended or adjusted under 35 U.S.C. 154(b) by 234 days.

(21) Appl. No.: 11/717,502

(22) Filed: Mar. 12, 2007

(65) Prior Publication Data
US 2007/0264336 A1 Nov. 15, 2007

Related U.S. Application Data

(63) Continuation of application No. 10/257,709, filed as application No. PCT/GB01/01726 on Apr. 12, 2001, now abandoned.

(30) Foreign Application Priority Data

Apr. 14, 2000 (IT) .............................. MI2000A0852
Sep. 7, 2000 (IT) .............................. MI2000A1963

(51) Int. Cl.
*A61K 31/40* (2006.01)
*A61K 9/20* (2006.01)
*A61K 9/22* (2006.01)
*A61K 9/24* (2006.01)
(52) U.S. Cl. ......... 424/464; 424/468; 424/472; 514/418
(58) Field of Classification Search .................. 424/400, 424/464, 468, 472; 514/418
See application file for complete search history.

(56) References Cited

U.S. PATENT DOCUMENTS

| 3,065,143 | A | | 11/1962 | Christenson et al. ........... 167/82 |
| 4,160,020 | A | | 7/1979 | Ayer et al. |
| 4,369,172 | A | | 1/1983 | Schor et al. ..................... 424/19 |
| 4,389,393 | A | | 6/1983 | Schor et al. ..................... 424/19 |
| 4,756,911 | A | | 7/1988 | Drost et al. ................... 424/468 |
| 4,824,860 | A | * | 4/1989 | Owen ............................. 514/48 |
| 4,839,177 | A | | 6/1989 | Colombo et al. ............. 424/482 |
| 4,865,849 | A | | 9/1989 | Conte et al. .................... 424/466 |
| 4,946,685 | A | | 8/1990 | Edgren et al. ................. 424/472 |
| 5,126,145 | A | | 6/1992 | Evenstad et al. |
| 5,213,808 | A | | 5/1993 | Bar-Shalom et al. ......... 424/473 |

(Continued)

FOREIGN PATENT DOCUMENTS

EP 0 113 964 B1 7/1984

(Continued)

OTHER PUBLICATIONS

Dimitriu, S., "Polysaccharides in Medical Applications", Marcel Dekker, Inc., pp. 730-754 (1996).

(Continued)

*Primary Examiner* — Taylor Victor Oh
(74) *Attorney, Agent, or Firm* — Mintz Levin Cohn Ferris Glovsky and Popeo, P.C.; David E. Johnson, Esq.; Muriel Liberto, Esq.

(57) ABSTRACT

An oral dosage form comprising a pharmaceutical tablet of one or more layers, one of which carries a biologically active substance; the formulation of said tablet includes different percentages of hydrophilic and lipophilic polymeric materials, and adjuvant substances. The tablets of the present invention show a release rate which is independent from the amounts of active substance present in the tablet.

35 Claims, 5 Drawing Sheets

U.S. PATENT DOCUMENTS

| | | | |
|---|---|---|---|
| 5,326,570 A | 7/1994 | Rudnic et al. | 424/458 |
| 5,395,626 A | 3/1995 | Kotwal et al. | 424/472 |
| 5,407,686 A | 4/1995 | Patel et al. | 424/468 |
| 5,422,121 A | 6/1995 | Lehmann et al. | 424/464 |
| 5,422,123 A | 6/1995 | Conte et al. | 424/479 |
| 5,487,901 A | 1/1996 | Conte et al. | 424/472 |
| 5,496,836 A * | 3/1996 | Di Rocco et al. | 514/370 |
| 5,510,114 A | 4/1996 | Borella et al. | 424/452 |
| 5,620,705 A | 4/1997 | Dong et al. | 424/472 |
| 5,626,874 A | 5/1997 | Conte et al. | 424/464 |
| 5,645,858 A | 7/1997 | Kotwal et al. | 424/495 |
| 5,650,169 A | 7/1997 | Conte et al. | 424/472 |
| 5,738,874 A | 4/1998 | Conte et al. | 424/472 |
| 5,780,057 A | 7/1998 | Conte et al. | 424/468 |
| 5,807,570 A | 9/1998 | Chen et al. | |
| 5,955,104 A | 9/1999 | Momberger et al. | 424/458 |
| 6,027,748 A | 2/2000 | Conte et al. | |
| 6,149,940 A | 11/2000 | Maggi et al. | 424/472 |
| 6,183,779 B1 | 2/2001 | Ouali et al. | 424/472 |
| 6,217,905 B1 | 4/2001 | Edgren et al. | 424/473 |
| 6,218,421 B1 | 4/2001 | King | 514/421 |
| 6,531,151 B1 | 3/2003 | Besse | 424/464 |
| 2010/0003320 A1* | 1/2010 | Vergnault et al. | 424/472 |

FOREIGN PATENT DOCUMENTS

| | | |
|---|---|---|
| EP | 0 133 964 A1 | 7/1984 |
| EP | 0 226 884 A2 | 7/1987 |
| EP | 0 299 602 A2 | 1/1989 |
| EP | 0 300 614 A1 | 1/1989 |
| EP | 0 384 514 A2 | 8/1990 |
| EP | 0 432 607 A1 | 6/1991 |
| EP | 0 432 607 B1 | 6/1991 |
| EP | 0 527 835 B1 | 10/1994 |
| EP | 0 624 373 A1 | 11/1994 |
| EP | 0 656 204 B1 | 6/1995 |
| EP | 0 663 820 B1 | 7/1995 |
| EP | 0 788 790 A2 | 8/1997 |
| EP | 0 795 324 A2 | 9/1997 |
| JP | 4-360826 | 12/1992 |
| JP | 2772695 | 4/1998 |
| WO | WO 91/16306 | 10/1991 |
| WO | WO 92/00735 | 1/1992 |
| WO | WO 93/23035 | 11/1993 |
| WO | WO 94/06416 | 3/1994 |
| WO | WO-9639136 A1 | 12/1996 |
| WO | WO 97/03670 | 2/1997 |
| WO | WO-9703670 A1 | 2/1997 |
| WO | WO 97/48385 | 12/1997 |
| WO | WO 98/00115 | 1/1998 |
| WO | WO 98/30208 | 7/1998 |
| WO | WO-9949852 A1 | 10/1999 |
| WO | WO 99/62496 | 12/1999 |
| WO | WO 02/11702 A2 | 2/2002 |

OTHER PUBLICATIONS

DrugBank, "Theophylline", Acc. No. DB00277, http://www.drugbank.ca/cgi-bin/getCard.cgi?CARD=%20DB00277, pp. 1-30, Jun. 13, 2005.

DrugBank, "Ursodeoxycholic acid", Acc. No. DB01586, http://www.drugbank.ca/cgi-bin/getCard.cgi?CARD=%20DB01586, pp. 1-8, Aug. 29, 2007.

DrugBank, "Prednisolone", Acc. No. DB00860, http://www.drugbank.ca/cgi-bin/getCard.cgi?CARD=%20DB00860, pp. 1-13, Jun. 13, 2005.

DrugBank, "Carbamazepine", Acc. No. DB00564, http://www.drugbank.ca/cgi-bin/getCard.cgi?CARD=%20DB00564, pp. 1-14, Jun. 13, 2005.

DrugBank, "Diclofenac", Acc. No. DB00586, http://www.drugbank.ca/cgi-bin/getCard.cai?CARD=%20DB00527, pp. 1-19, Jun. 13, 2005.

DrugBank, "Omeprazole", Acc. No. DB00338, http://www.drugbank.ca/cgi-bin/getCard.cgi?CARD=%20DB00338, pp. 1-11, Jun. 13, 2005.

Gennaro et al., in Remington's Pharmaceutical Sciences, 18$^{th}$ Ed., Mack Publishing Company, Easton, PA, Ch. 19, p. 304 (1990).

GlaxoSmithKline, "PAXIL®", http://us.gsk.com/products/assets/us_paxil.pdf, pp. 1-43, Jun. 2008.

Griffin, W.C., "Classification of Surface-Active Agents by 'HLB'", *J. Soc. Cosmetic Chem.*, 1:311-326 (1949).

Handbook of Pharmaceutical Excipients, 3$^{rd}$ Ed., Kibbe, Ed., American Pharmaceutical Assoc., pp. 86-91, 94-95, 142-145, 146-153, 228-229, 252-255, 276-285, 304-309, 316-319, 324-329, 392-399, 416-419, 432-439, 486-489, 500-585 (1986).

"Hydroxypropyl Methylcellulose", *U.S. Pharmacopeia*, The National Formulary, U.S. Pharmacopeial Convention, National Publishing Philadelphia, pp. 843-844 (1999).

Dumitriu, S., "Polysaccharides in Medical Applications", Marcel Dekker, Inc., pp. 730-754 (1996).

DrugBank: showing Theophylline, Primary Accession No. DB00277 http://www.drugbank.ca/cgi-bin/getCard.cgi?CARD=DB00277, pp. 1-28, Jun. 13, 2005.

DrugBank: showing Ursodeoxycholic acid, Primary Accession No. DB01586, http://www.drugbank.ca/cgi-bin/getCard.cgi?CARD=DB01586, pp. 1-7, Aug. 29, 2007.

DrugBank: showing Prednisolone, Primary Accession No. DB00860, http://www.drugbank.ca/cgi-bin/getCard.cgi?CARD=DB00860, pp. 1-12, Jun. 13, 2005.

DrugBank: showing Carbamazepine, Primary Accession No. DB00564, http://www.drugbank.ca/cgi-bin/getCard.cgi?CARD=DB00564, pp. 1-12, Jun. 13, 2005.

DrugBank: showing Diclofenac, Primary Accession No. DB00586, http://www.drugbank.ca/cgi-bin/getCard.cgi?CARD=DB00527, pp. 1-16, Jun. 13, 2005.

DrugBank: showing Omeprazole, Primary Accession No. DB00338, http://www.drugbank.ca/cgi-bin/getCard.cgi?CARD=DB00338, pp. 1-10, Jun. 13, 2005.

DrugBank: showing Diclofenac (DB00586, Primary Accession No. DB00586, http://www.drugbank.ca/cgi-bin/getCard.cgi?CARD=DB00586, pp. 1-16 (2005).

Conte, U. and Maggi, L., "Multi-layer tablets as drug delivery devices", *Pharmaceutical Technology Europe*, pp. 18, 20, 22 24 and 25, Feb. 1998.

Opposition filed by Maiwald on Apr. 21, 2009, and received at the EPO on Apr. 21, 2009, via facsimile, Re Application No. 01 921 605.0, (EP Patent 1 272 167), 16 pages.

Analytical Profiles of Drug Substances, Ed. Klans Florey, Academic Press Inc., 18:228-229 (1989).

Ballard, Berton E., "Prolonged-Action Pharmaceuticals", *Remington's Pharmaceutical Sciences*, Chapter 91.

Boles et al., "Design and evaluation of a sustained release aminophylline tablet", *Drug Development and Industrial Pharmacy*, 19(3):340-370 (1993).

Lordi, Nicholas J., "Sustained Release Dosage Forms", *The Theory and Practice of Industrial Pharmacy*, 3$^{rd}$ ed., eds. Lachman, Lieberman and Kanig, Lea & Febiger, Chapter 14, 2009.

Martindale: The Complete Drug Reference—Monographs, The Pharmaceutical Press, pages relating to nifedipine and ketoprofen, 2000.

Study 166, phase II clinical trial, which ran from Nov. 1, 2000 to Oct. 3, 2001, available on http://ctr.gsk.ci/uk/summary/ropinirole/strudylist.asp.

Web page from "Drug Bank" at http://redpoll.pharmacy.ualberta.ca/drugbank, 2007.

"Ropinirole prolonged release: a guide to its use in Parkinson's disease", *Drugs and Therapy Perspectives*, 25(6):1-5 (2009).

Edin et al., "Adherence among patients with Parkinson's disease taking ropinirole immediate release at least three times daily", 12th International Congress of Parkinson's disease and Movement Disorders, Chicago, IL, USA (Jun. 22-26, 2008).

Kaye and Nicholls, "Clinical Pharmacokinetics of Ropinirole", *Clin. Pharmacokinet.*, 39(4):243-254 (2000).

Kulkarni et al., "Medication Adherence and Associated Outcomes in Medicare Health Maintenance Organization-Enrolled Older Adults with Parkinson's Disease", *Mov. Dis.*, 23:359-365-365 (2008).

Lee and Kim, "Probing the mechanisms of drug release from hydrogels", *J. Controlled Release*, 16:229-236 (1991).

Longer and Robinson, "Sustained-Release Drug Delivery Systems", in *Remington's Pharmaceutical Sciences*, 18th Ed, Ch. 91, pp. 1676-1693 (1990).

Obeso et al., "Review—The Role of Pulsatile Versus Continuous Dopamine Receptor Stimulation for Functional Recovery in Parkinson's Disease", *Eur. J. Neurosci.*, 6:889-897 (1994).

Pahwa et al., "Ropinirole 24-hour prolonged release. Randomized, controlled study in advanced Parkinson disease", *Neurology*, 68:1108-1115 (2007).

Patentee's Response to Opposition for European Patent No. EP-B-1272167, Nov. 2009.

Print out from http://www.addebook.com/biomed/html/2009/handbook-of-pharmaceutical-controlled-release-technology 16875.htm downloaded on Oct. 21, 2009, *Handbook of Pharmaceutical Controlled Release Technology*, (Aug. 15, 2000).

Rascal et al., "A Five-Year Study of thje Incidence of Dyskinesia in Patients with Early Parkinson's Disease Who Were Treated With Ropinirole or Levodopa", *N. Eng. J. Med.*, 342:1484-1491 (2000).

Ruzicka et al., "Maintained increase in "on" time with ropinirole prolonged release in advanced Parkinson's disease", 3rd World Congress on Controversies in Neurology, Prague, Czech Republic, (Oct. 8-11, 2009).

Summary of Product Characteristics for Requip® dated Aug. 10, 2000.

Summary of Product Characteristics for Requip® dated Dec. 21, 1998.

Szczudlik et al., "Long term safety and patient preference for dose frequency in patients receeiving ropinirole prolonged release in early or advanced Parkinson's disease", 19th Annual Meeting of the European Neurological Society, Milan, Italy, (Jun. 20-24, 2009).

Tompson and Vearer, "Steady-State Pharmacokinetic Properties of a 24-Hour Prolonged-Release Formulation of Ropinirole: Results of Two Randomized Studies in Patients with Parkinson's Disease", *Clin. Ther.*, 29(12):2654-2666 (2007).

Venkatraman et al., An Overview of Controlled Release Systems, in *Handbook of Pharmaceutical Controlled Release Technology*, Ch. 22, Wise, Ed., Marcel Dekker, Inc., New York, pp. 431-463 (2000).

Response to Communication received from Opposition Division from the European Patent Office dated Aug. 15, 2010 for European counterpart Patent No. 1272167.

*Handbook of Pharmaceutical Excipients*, Fifth Edition, Rowe Ed., Pharmaceuticals Press and American Pharmacists Association, pp. 278-282 (2006).

Decision of the Opposition Division of the European Patent Office in connection with the European Opposition in EP 1272167 dated Nov. 16, 2010.

Minutes of the oral proceedings in connection with the European Opposition in EP 1272167 dated Nov. 16, 2010.

* cited by examiner

PLAN

SIDE

END

CROSS-SECTION
THROUGH LINE X - X

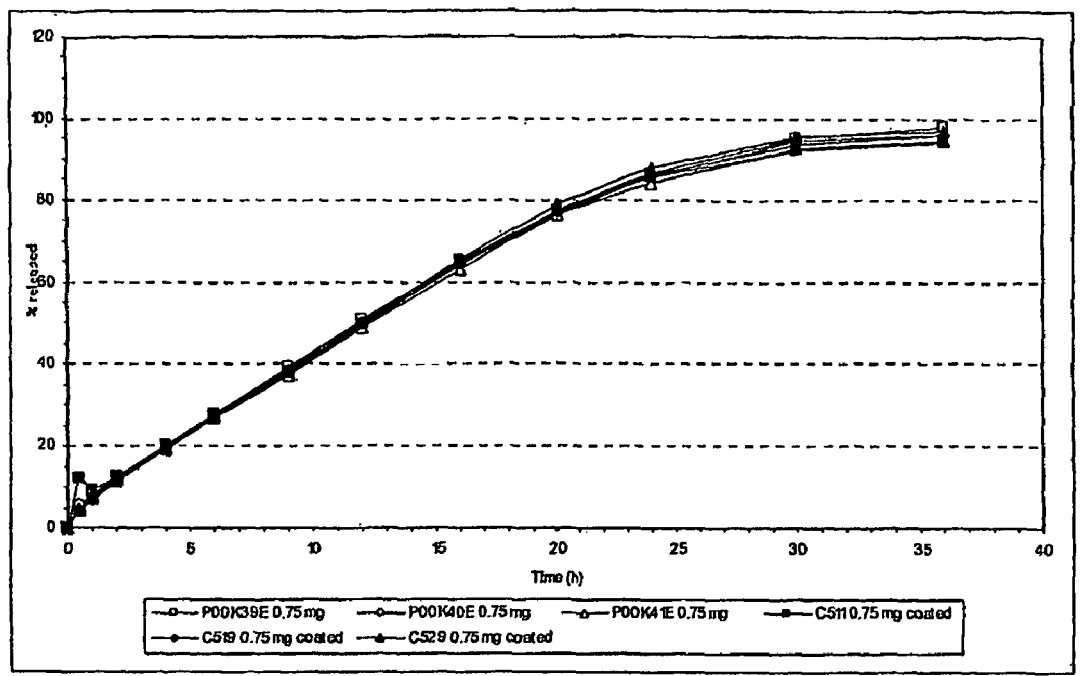
FIGURE 10: Dissolution profile comparison, replication batches, dosage 0.75 mg
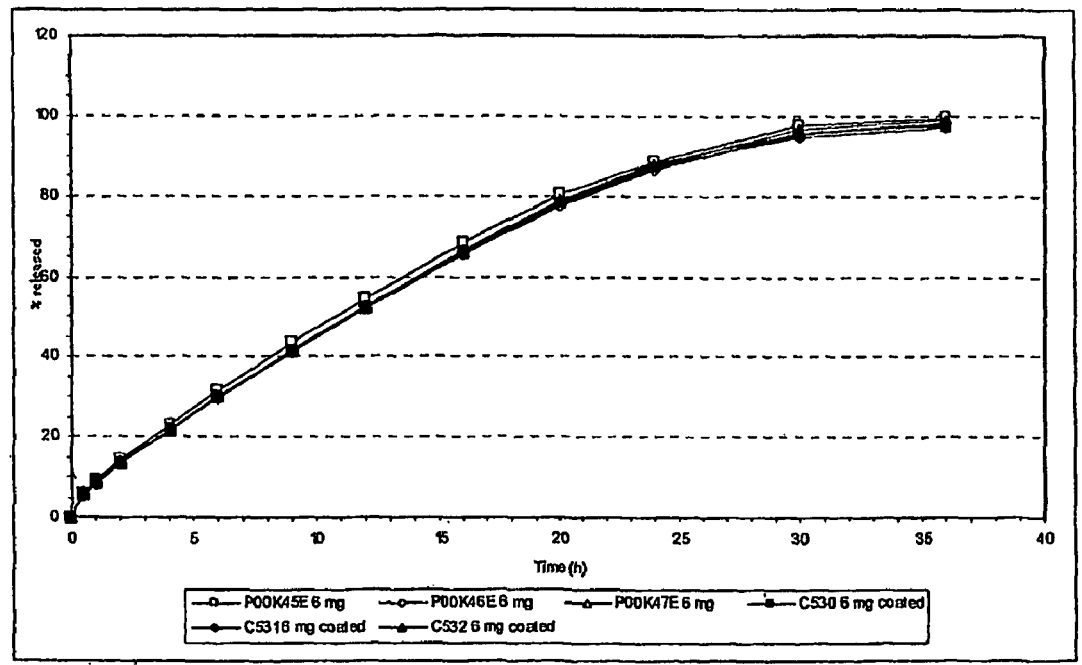
FIGURE 11: Dissolution profile comparison, replication batches, dosage 6 mg

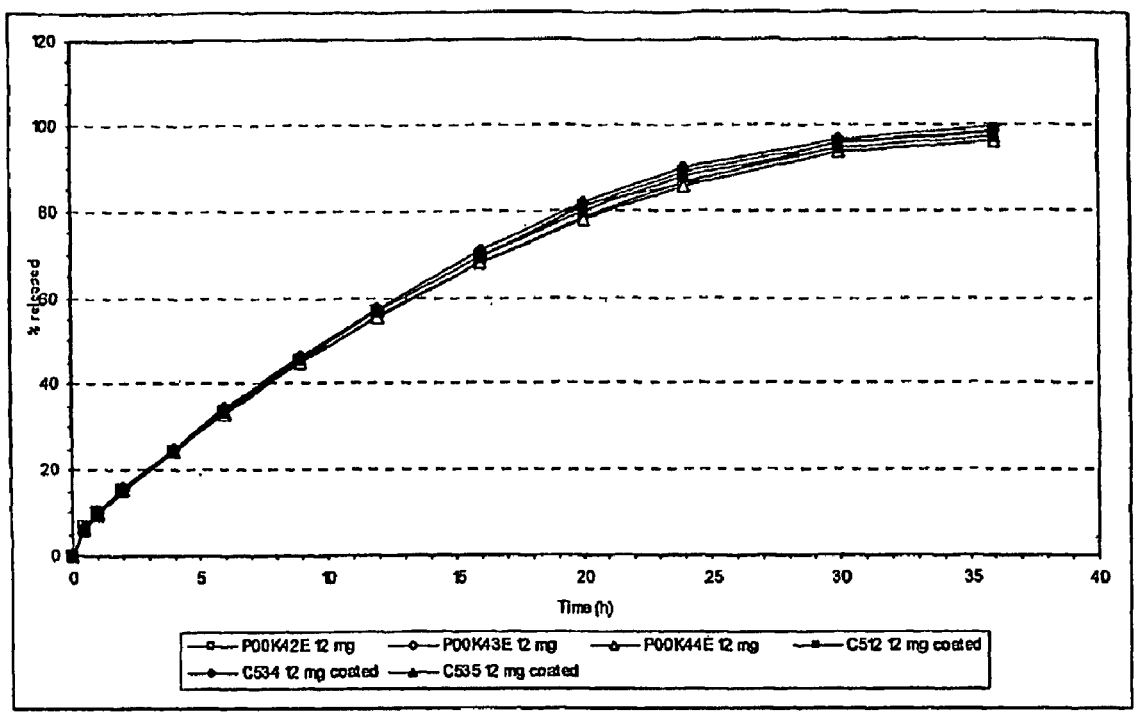
FIGURE 12: Dissolution profile comparison, replication batches, dosage 12 mg
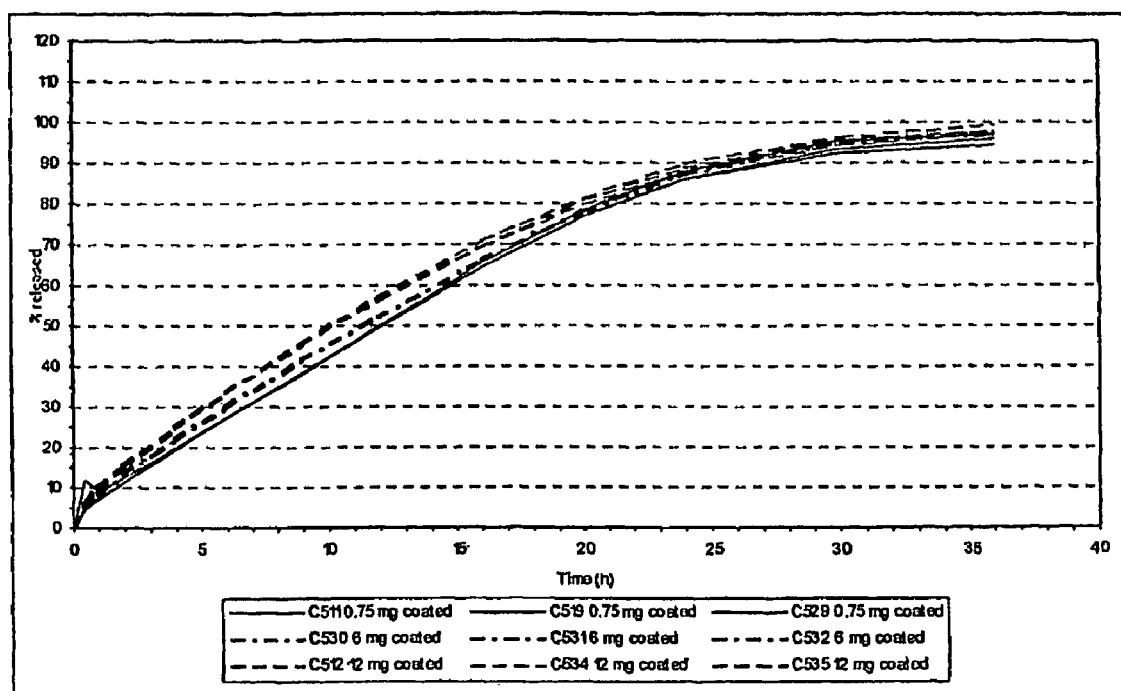
FIGURE 13: Dissolution profile comparison, replication batches, all dosages

HYDROPHILIC/LIPOPHILIC POLYMERIC MATRIX DOSAGE FORMULATION

RELATED APPLICATIONS

This application claims priority to, and is a continuation application of, U.S. Ser. No. 10/257,709, filed Mar. 10, 2003 now abandoned, which is a National Stage application of PCT/GB01/01726 filed Apr. 12, 2001, and claiming priority to Italian patent application numbers MI2000A000852 and MI2000A011963 filed on Apr. 14, 2000 and Sep. 7, 2000 respectively, and hereby incorporated by reference in their entireties.

JOINT RESEARCH AGREEMENT

The claimed invention was made pursuant to a joint research agreement between Jagotec AG, Skyepharma AG and SmithKline Beecham (Cork) Limited.

The present invention relates to a dosage formulation or tablet comprising a mixed matrix of hydrophilic and lipophilic components able to control the release rate of one or more therapeutically active agents from the formulation/tablet.

Recent years have seen considerable efforts made in the pharmaceutical technology field of research aimed at preparing innovative pharmaceutical forms, meant for the administration of active substances, both in human treatment and the veterinary field. One of the fundamental aspects of the innovative qualities of pharmaceutical dosage forms and/or prepared formulation systems is the potential targeting the release of the drug (or the active substance) to a specific site of action and/or of releasing such active substances with an a priori programmable velocity which can be assessed by way of suitable "in vitro" tests.

Other sectors are also interested in these technical fields, not just the human health sector, namely veterinary and agricultural sectors, especially with regard to the controlled release of fertilisers, weedkillers, insecticides and/or specific protection agents for certain cultures.

There are many examples in the pharmaceutical sector which describe the preparation of pharmaceutical forms capable of releasing the active principle (active substance) with zero kinetics. As is well known to experts in the field, this means that the active principle carried is given up by the pharmaceutical form at a constant velocity through time and for a programmable time period. In particular, the release of a drug can be expressed by the following empirical relation:

$$M_t/M_0 = Kt^n$$

the fraction of drug released ($M_t/M_0$) is proportional to a constant K which depends on the diffusion coefficient in the matrix, whereas the constant n depends on the swelling characteristics and the relaxation velocity of the polymeric chains on the swelling front. There are many examples of such pharmaceutical forms, for example, is quoted in the volume of S. Dimitriu "Polysaccharides in medical applications" M. Dekker, New York 1996.

There are many examples and pharmaceutical applications that concern dosage forms utilisable for different administration forms namely oral, transdermal, vaginal and ocular. Certainly, given the extreme importance and the widespread use of oral drug administration, the more numerous and differentiated embodiments are those aimed at releasing the active principle in the gastrointestinal tract, for example, the OROS system described in U.S. Pat. No. 4,160,020.

Further progress in this field is also provided by the pharmaceutical oral dosage forms described in U.S. Pat. Nos. 4,839,177 and 5,422,123 (equivalent to EP-A-0226884 and EP-A-0432607 respectively) which describes the preparation of pharmaceutical forms for oral use capable of guaranteeing the liberation of an active principle at a constant release velocity, i.e. according to zero kinetics (n=0 in the above formula). In particular, these documents describe the preparation of a therapeutic system consisting, in its simplest form, a hydrophilic matrix containing a drug and suitable excipients, capable of allowing the release of the active principle at varied rates (i.e. at controlled rates of release).

Constituent components important in causing the slowed release of the active principle are the hydrophilic polymers, which may be gellable, and are capable of swelling upon contact with water and/or aqueous fluids, forming a gelled layer from which the active principle spreads according to Fickian type kinetics.

The therapeutic system described above in U.S. Pat. Nos. 4,839,177 and 5,422,123 is characterised in that one part of said matrix is covered by an impermeable barrier (obtained by the application of a polymeric film which is insoluble in water and aqueous medium as in U.S. Pat. No. 4,839,177 or in that a layer of material and/or a polymeric material mix is applied by compression (possibly granulates obtained in accordance with known techniques) thus giving impermeability and/or, in any case, impeding the release of the drug carried in the matrix form the protected surface for a predeterminable time period (as in U.S. Pat. No. 5,422,123). The result is that the release of the active principle carried in the hydrophilic matrix only occurs from the free surface of the layer containing the active substance in direct contact with the dissolution medium. Such a system is characterised in that the active principle, carried in said pharmaceutical forms, is given up at a velocity which generally proves constant over time (zero release kinetics) as is highlighted in the claims of the cited patent.

Other tablet formulations have provided for the liberation of one or more drugs at different release rates (WO 94/06416) by appropriate formulation of the layers in the multi-layer tablet. Alternative phased drug release systems have described the use of an impermeable membrane to control the time of drug release (U.S. Pat. No. 5,487,901), a complete coat of a biodegradable polymeric material (U.S. Pat. No. 6,027,748), or a more substantial layer of controlled permeability materials (EP-A-0788790). Still further multi-layer tablets have been described in which the tablet shows a high volume increase on contact with the contents of the stomach so as to provide for prolonged gastric residence times (EP-A-0795324).

However, in many treatment protocols, the patient must take drugs for extended time periods, for chronic disease treatment and must follow, at times, complex posological patterns, taking two or more pharmaceutical forms over 24 hours. Such complex and distinct therapeutic models are poorly supported and infrequently followed by non-hospitalised patients; in fact, the withdrawal of the correct observance of the posological models is very frequent and well known in the case of outpatients, and such a withdrawal is directly proportional to the complexity and number of administrations required or recommended during the day. For example, in the treatment of chronic diseases, for example hypertension the posology of the drugs must be adjusted in relation to the seriousness of the pathology and hence personalised to the specific therapeutic needs of the individual concerned.

Of importance to many pathological models, is the request by the medical profession to make available pharmaceutical forms with a very differentiated active principle content (so as to favour the personalisation of the posology), which however are able to release the drug with similar or equivalent velocity and release kinetics, independent from the amount of active substance carried.

Therefore the availability of pharmaceutical forms which can release different dosages of the same drug at the same or similar velocity would provide the medical profession with a solution, to an important therapeutic problem, of major social relevance for the type of therapy at which it is directed. Such dosage forms would allow for the optimisation of drug use and biologically active substances in general.

It has now been discovered that utilising a particular formulation and pharmaceutical form consisting of a multi-layer tablet, preferably containing two or three layers, it is possible to obtain a similar or identical release velocity, even if said tablet carries very different amounts of the same active substance.

The originality of the new, prepared embodiment, in addition to the morphological and practical characteristics of the new therapeutic system are better illustrated in the following detailed description.

According to a first aspect of the invention there is provided a multi-layer tablet, in particular a multi-layer controlled-release tablet, comprising:

(a) one active layer containing: (i) an active substance, (ii) hydrophilic polymeric substances which swell and/or gel and/or erode upon contact with aqueous liquids, (iii) lipophilic substances, and (iv) adjuvant substances, wherein the weight ratio of the hydrophilic polymeric substances to the lipophilic substances contained in said active layer is in the range of 10:1 to 0.5:1; and (b) one or more barrier layers containing one or more of: hydrophilic polymeric substances which swell and/or gel and/or erode upon contact with aqueous liquids, lipophilic substances, and adjuvant substances.

Multi-layer tablets prepared in accordance with the present invention are able to provide substantially equivalent (or identical) release kinetics for the same active substance when formulated at different amounts in the active substance containing layer in the multi-layer tablet. The pharmaceutical tablets of the invention have the advantage of releasing the carried active substance in a programmed way, preferably also avoiding the phenomenon of dose dumping, and therefore being able to meet specific therapeutic needs with the gradual and controlled release of the active substance.

The multi-layer tablets of the present invention can be prepared as two-layer tablets, three-layer tablets or greater numbers of layers if required. At least one layer will contain the active substance to be released from the tablet and least one layer will be a barrier or support layer with respect to the active substance containing layer. Possible constructions of multi-layer tablets are shown in FIGS. 1 to 9. The tablets may have an overall substantially circular cross-section, or it may adopt a more oval cross-section or any other suitable geometric shape, for example rectilinear. The tablet may also be shaped as a caplet (capsule form tablet). As will be appreciated there are many potential arrangements of the layers in multi-layer tablets.

The layer containing the active substance can be referred to as the active layer, although, it should be noted that more than one active substance can be formulated in a tablet of the present invention. The layer that generally does not contain an active substance can be referred to as a barrier layer or a support layer.

A simple two-layer tablet is shown in FIG. 1 where one lateral surface of the active substance containing layer (dotted) is covered by a barrier layer (hatched). A variation of this construction is shown in FIG. 2 where two barrier layers cover both exposed lateral surfaces of the active substance containing layer. In FIG. 3 a single barrier layer coats one lateral surface and the side of the active layer. The barrier layer is shown as being present in the form of an annular ring in FIG. 4 surrounding the active core and FIG. 5, an active core consisting of two active layers is shown surrounded by an annular ring of a barrier layer.

In FIG. 6 a three layer tablet is shown in which there is a first barrier layer (3) with an exposed upper lateral surface and sides, which is adjacent to a second active layer (2) with both lateral surfaces covered and the side of the layer exposed, which is in turn adjacent to a second active layer (1) where the bottom lateral surface is exposed and the side is exposed. The two active layers may contain different active substances or the same active substance in different amounts. FIG. 7 shows an alternative arrangement of the FIG. 6 embodiment, where the active substance layer (5) is wholly within the barrier layer (6) and the second active substance layer (4). In FIG. 8, a similar three-layer tablet is shown in which the barrier layer (8) is interposed between the two active substance containing layers (9) and (7).

Another three layer tablet (caplet) construction is also shown in FIG. 9 in which the tablet has two external barrier layers (10, 12) and an active substance layer (11) interposed between the barrier layers.

In some tablet configurations, the barrier layer may also contain an active substance such that it acts as a barrier layer with respect to a first active substance containing layer, but which itself is an active substance containing layer. Generally, in such embodiments, the active substance in the active layers is different in the separate layers, although arrangements in which the same active is present in the separate active layers in different amounts can also be envisaged.

The barrier layer(s) are meant to limit the release surface of the active layer, so as to allow that said carried active substance is released by the sole uncovered surface upon contact with the dissolution medium and/or the biological fluids according to kinetics that, in vitro, can be programmed according to precise methods, as will be highlighted in the given examples of the present invention.

Any pharmaceutically active substance suitable for oral administration in the form of a tablet can be formulated in a tablet of the present invention. An active substance is therefore a pharmaceutical (drug) with a therapeutic use, such substances also include those for administration for non-therapeutic uses, such as diagnosis of for dietary purposes.

Preferably the active substance may be one aimed at the treatment of chronic diseases, for example, drugs acting on the cardiovascular system, anti-arrhythmics, cardiac stimulants, vasodilators, calcium antagonists, anti-hypertensives, for example anti-adrenergic substances of central and peripheral action or substances acting on the arteriolar musculature, analgesic substances, substances acting on the renin-angiotensin system, anti-hypertensives and diuretics in association, anti-Parkinson's Disease agents, diuretics and drugs for the treatment of Alzheimer's disease, anti-histamines and/or anti-asthmatics.

Examples of active substances which may be used in such pharmaceutical forms are: propranolol, atenolol, pindolol, ropinirole, prazosin, ramipril, spirapril; spironolactone, metipranolol, molsidomine, moxonidina, nadolol, nadoxolol, levodopa, metoprolol, timolol. In a particular preferred embodiment, the active substance (i) comprises or is ropinirole, inclusive of pharmaceutically acceptable salts thereof.

Ropinirole, its chemical structure, processes for its preparation and therapeutic uses thereof, are more fully described in EP-A-0113964 (see Example 2), EP-A-0299602, EP-A-0300614, WO 91/16306, WO 92/00735 and WO 93/23035, and the contents of which are hereby incorporated by reference. "Ropinirole" as mentioned herein is defined as including pharmaceutically acceptable salts thereof. Most preferably, the ropinirole used in the tablet is in the form of the hydrochloride salt. Ropinirole is presently marketed as the HCl salt in an immediate-release tablet for the treatment of Parkinson's Disease (see also EP-A-0299602). Ropinirole can be synthesised by the advantageous method described in WO 91/16306.

In embodiments of the invention in which the active substance comprises or is ropinirole, the amount of ropinirole present, inclusive of pharmaceutically acceptable salts thereof, may be up to 12.0 mg, preferably from 0.75 mg to 12.0 mg, measured as the amount of ropinirole base present, that is excluding any amount of acid (for example, hydrochloric acid, HCl) added to form any ropinirole salts. The amount of ropinirole present, inclusive of pharmaceutically acceptable salts thereof, may be up to 12.0 mg, preferably from 0.75 mg to 12.0 mg, measured as the amount of ropinirole base present, per 150 mg of active layer present. See Examples 13 to 18 hereinafter.

Analgesic substances include, but are not limited to, steroidal anti-inflammatory drugs, opioid analgesics, and non-steroidal anti-inflammatory drugs (NSAIDs). The analgesic substance may be a non-steroidal anti-inflammatory drug (NSAID), such as acetyl salicylic acid, salicylic acid, indomethacin, ibuprofen, naproxen, naproxen sodium, flubiprofen, indoprofen, ketoprofen, piroxicam, diclofenac, diclofenac sodium, etodolac, ketorolac, or the pharmaceutically acceptable salts and/or derivatives or mixtures thereof.

Other suitable analgesic substances include, but are not limited to opioid analgesics such as alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil; tramadol, tilidine and pharmaceutically acceptable salts and/or derivatives or mixtures thereof.

Anti-hypertensive drugs may include, diltiazem, trapidil, urapidil, benziodarone, dipiridamole (dipyridamole), lidoflazine, naphthydrofuryl oxalate, perhexyline maleate, oxyfedrine hydrochloride. Anti-histamines and/or anti-asthmatics may include ephedrine, terfenadine, theophylline or chlorpheniramine.

In any case the matrices can be prepared, carrying any type of active principle for which pharmaceutical forms may be necessary capable of releasing also very different amounts of active substance with the same release kinetics.

In the tablets of the present patent application, the active substance to be carried may have a very wide solubility interval in water, e.g. between 0.01 mg/L up to 3000 g/L, preferably between 10 mg/L up to 1000 g/L (e.g. ropinirole has 133 g/L solubility), or between 0.01 mg/L up to 100 g/L.

The active substance is preferably contained in a percentage between 0.05% to 50% by weight of the active layer; more preferred ranges of the active substances are 0.05% to 40%, 0.05% to 30%, 0.05% to 10%, 0.05% to 20%.

Natural or synthetic hydrophilic polymeric substances, can be used in the preparation of said active layer which are biocompatible and/or biodegradable materials and pharmaceutically acceptable, e.g. polyvinylpyrrolidone in particular non-cross-linked polyvinylpyrrolidone (e.g. of molecular weight 30,000-400,000), hydroxypropylcellulose with a molecular weight of from 100,000 to 4,000,000, sodium carboxymethylcellulose (e.g. non-cross-linked, e.g. typical molecular weight 90,000-700,000), carboxymethylstarch, potassium methacrylate-divinylbenzene copolymer, hydroxypropylmethylcellulose with a molecular weight between 2,000 and 4,000,000, polyethyleneglycols of different molecular weight preferably between 200 and 15,000 (more preferably 1000-15000) and polyoxyethylenes of molecular weight up to 20,000,000 (more preferably 400,000-7,000,000), carboxyvinylpolymers, poloxamers (polyoxyethylene-polyoxypropylene copolymer), polyvinylalcohols, glucanes (glucans), carrageenans, scleroglucanes (scleroglucans), mannans, galactomannans, gellans, xanthans, alginic acid and derivatives (e.g. sodium or calcium alginate, propylene glycol alginate), polyaminoacids (e.g. gelatin), methyl vinyl ether/maleic anhydride copolymer, carboxymethylcellulose and derivatives (e.g. calcium carboxymethylcellulose), ethylcellulose, methylcellulose, starch and starch derivatives, alpha, beta or gamma cyclodextrin, and dextrin derivatives (e.g. dextrin) in general. The hydrophilic polymeric substance is therefore one which can be described as a controlled release polymer or a polymeric substance which is capable of achieving controlled release (CR).

More preferably for achieving advantageous controlled release of the active substance the hydrophilic polymeric substances in the active layer comprise one or more of the following: hydroxypropylcellulose with a molecular weight of from 100,000 to 4,000,000, hydroxypropylmethylcellulose (HPMC) with a molecular weight between 2,000 and 4,000,000 (more preferably between 10,000 and 1,500,000 molecular weight, still more preferably between 20,000 and 500,000 molecular weight, most preferably about 250,000 molecular weight), ethylcellulose or methylcellulose. The most preferred controlled release polymer is HPMC.

Hydrophilic polymeric substances such as sodium carboxymethylcellulose and/or calcium carboxymethylcellulose that act as viscosity-increasing agents/polymers or "cage-forming" components are also preferred components e.g. of the active layer. The provision of these viscosity-increasing polymers in the active layer is preferred because these help to reduce the "dose-dumping" effects occasionally seen with soluble active substances (e.g. ropinirole) whereby a significant minority of the active substance can be released from the active layer in the first (say) hour after oral administration. Thus, it is preferred for this purpose that the hydrophilic polymeric substances in the active layer comprise sodium carboxymethylcellulose, carboxymethylcellulose or a derivative (e.g. calcium carboxymethylcellulose), hydroxypropylcellulose with a molecular weight of from 100,000 to 4,000,000, a carboxyvinylpolymer, a carrageenan, a xanthan, alginic acid or a derivative (e.g. sodium or calcium alginate, propylene glycol alginate), ethylcellulose, methylcellulose, dextrin and/or maltodextrin. Most preferred for this purpose is sodium carboxymethylcellulose (NaCMC) (e.g. non-cross-linked, e.g. typical molecular weight 90,000-700,000). The present invention also comprehends the use of other equivalent polymers able to act as viscosity-increasing agents and/or "cage-forming" components.

It is more preferred that the hydrophilic polymeric substances in the active layer comprise both the above-mentioned preferred controlled release polymers and the above-defined viscosity-increasing polymers. Thus it is preferred that the hydrophilic polymeric substances in the active layer comprise:

(a) one or more of the following: hydroxypropylcellulose with a molecular weight of from 100,000 to 4,000,000, hydroxypropylmethylcellulose (HPMC) with a molecular weight between 2,000 and 4,000,000, ethylcellulose or methylcellulose; and (b) sodium carboxymethylcellulose, carboxymethylcellulose or derivatives (e.g. calcium carboxymethylcellulose), hydroxypropylcellulose with a molecular weight of from 100,000 to 4,000,000, a carboxyvinylpolymer, a carrageenan, a xanthan, alginic acid or a derivative (e.g. sodium or calcium alginate, propylene glycol alginate), ethylcellulose, methylcellulose, dextrin and/or maltodextrin.

Thus, while the controlled release polymer (a) such as HPMC is still swelling and/or gelling gradually in the first hour or so after oral administration of the tablet, when it may be less effective in controlling release of soluble active substances such as ropinirole from the active layer, the viscosity-increasing polymer (b) such as sodium carboxymethylcellulose (NaCMC) reduces the release of the active substance from the active layer. Without being bound by theory, ionic viscosity-enhancers like NaCMC might also to interact with the hydroxypropyl groups of, for example, HPMC to boost synergistically the hydration and swelling rate of HPMC leading to greater gel strength.

Thus, the most preferred combination is that the hydrophilic polymeric substances in the active layer include (or are) HPMC and sodium carboxymethylcellulose, especially when the active substance has a high (e.g. from 10 mg/L to 1000 g/L) solubility in water, such as ropinirole.

Preferably, the hydrophilic polymeric substances have an HLB value of at least 10 (see A. Gennaro and J. Remington, Remington's Pharmaceutical Sciences, 18$^{th}$ edition, Mack Publishing Company, Easton, Pa., 304 (1990) and W. C. Griffin, J. Soc. Cosmetic Chemists, vol. 1, page 311, 1949 for HLB values and measurement thereof). Said hydrophilic polymeric substances make up between 1% and 75% of the weight of the active layer, but preferably are present in a percentage between 5% and 65% and/or between 30 and 75%, more preferably 43-75% or 43-67% or 43-65%. Any HPMC present in the active layer is preferably present in about 40-63% by weight of the active layer. The viscosity-increasing polymers mentioned above, such as sodium carboxymethylcellulose, if present are preferably present in up to 20% by weight of the active layer, more preferably (especially for NaCMC) 3-20%, 5-20%, 7-15%, or about 10% by weight of the active layer.

For all the polymers cited different types are commercially available characterised by different chemical, physical, solubility and gelification properties. In particular, as regards, hydroxypropylmethylcellulose various types with a different molecular weight (between 1,000 and 4,000,000, preferably from 2,000 to 4,000,000, even more preferably between 10,000 and 1,500,000 molecular weight, still more preferably between 20,000 and 500,000 molecular weight, most preferably about 250,000 molecular weight) can be used and with different degrees of substitution. Said types of hydroxypropylmethylcellulose have differentiated characteristics being mainly erodible or able to be gelled, depending on the viscosity and the degrees of substitution (D.S.) present in the polymeric chain. Gellable HPMCs (e.g. Methocel K grades) are preferable to erodible HPMCs (e.g Methocel E grades). The polyethyleneglycols and polyoxyethylenes show identical behaviour: in fact, different hydrophilic and gelification properties correspond to different molecular weights.

The molecular weight of polymers and the 2% viscosity of polymers can be directly correlated ("METHOCEL™ in Aqueous Systems for Tablet Coating", page 12, published by The Dow Chemical Company—www.dow.com—METHOCEL™ is a trademark of The Dow Chemical Company) where viscosity of a polymer is defined as viscosity of a 2% aqueous solution at 20° C. measured as mPa.seconds. Viscosity is measured in Pascal seconds (SI units) or in poise (c.g.s. units), where 1 centipoise=$10^{-3}$ Pa.sec. So for example, METHOCEL™ K100M has an approximate molecular weight of 246,000 and a corresponding 2% viscosity of 100,000 mPa.sec (based on an average viscosity of 80,000 to 120,000 mPa.sec.); METHOCEL™ K4M has an approximate molecular weight of 86,000 and a corresponding 2% viscosity of 4,000 mPa.sec; and METHOCEL™ K100LV has an approximate molecular weight of 27,000 and a corresponding 2% viscosity of 100 mPa.sec. For this reason, the preferred molecular weight ranges of the polymeric substances, for example the hydroxypropylmethylcellulose polymers can also be defined in terms of viscosity.

One preferred viscosity range for the hydroxypropylmethylcellulose polymers as defined above may be in the range of from 50 to 150,000 mPa.sec, suitably 80,000 to 120,000 mPa.sec (e.g. K100M, as in the active and barrier layers of Examples 13-21). This applies both to the active layer (discussed above) or the barrier/support layer(s) (discussed below).

In an alternative embodiment, in order to obtain a faster release rate, the viscosity range for the hydroxypropylmethylcellulose polymers in the active and/or barrier layer(s) may be in the range of from 50 to 25,000 mPa.sec (including Methocels K4M, K15M, K100LV). In this embodiment, preferably some or all of the HPMC polymers have a viscosity in the range of from 1000 to 25,000 mPa.sec (including Methocels K4M & K15M but not K100LV or K100M). More preferably, HPMC polymers having a viscosity in the range of from 1000 to 25,000 mPa.sec are present in the active or barrier layer in a percentage of from 5 to 50% by weight of the active or barrier layer. In particular, Examples 22 and 23 hereinafter have 10% and 40 weight % respectively of such HPMC (K4M) in their barrier layers which gives a slightly faster release profile in vitro than the ca. 45 wt % K100M HPMC present in the barrier layers of Examples 13-18 and 19-21, as inter alia the active substance e.g. ropinirole migrates faster through the barrier layers. Preferably, the proportion of low-viscosity HPMCs having from 50 to <1000 mPa.sec viscosity (including Methocel K100LV) contained in the active or barrier layers is less than 30% by weight of that layer—e.g. Example 22 has 20 wt % of such HPMC (K100LV) as well as 10 wt % K4M HPMC in the barrier layer. Up to 30% low-viscosity HPMC in active or barrier layer can increase water uptake and aid gelling, increasing the matrix viscosity and decreasing the release rate, but greater amounts are not preferred.

In an alternative embodiment of the invention, there is provided a tablet as previously defined, in which the active layer contains polymeric material with slow swelling and/or gelification and/or erosion and/or solubility properties.

A fundamental characteristic of the tablets of the present invention is that, for the formulation both of the layer containing the active substance and the barrier layers, lipophilic substances are utilised, for example natural fats (coconut, soya, cocoa) as such or totally or partially hydrogenated, beeswax, polyethoxylated beeswax, mono-, bi- and tri-substituted glycerides, glyceryl palmitostearate, glyceryl behenate (glyceryl tribehenate $C_{69}H_{134}CO_6$, e.g. Compritrol 888, where behenic acid=docosanoic acid $C_{21}H_{43}COOH$), diethyleneglycol palmitostearate, polyethyleneglycol stearate, polyethyleneglycol palmitostearate, polyoxyethylene-glycol palmitostearate, glyceryl monopalmitostearate, cetyl palmitate, mono- or di-glyceryl behenate (glyceryl mono-behenate or glyceryl di-behenate), fatty alcohols associated with polyethoxylate fatty alcohols, cetyl alcohol, stearic acid, saturated or unsaturated fatty acids and their hydrogenated derivatives, hydrogenated castor oil and lipophilic substances in general. In certain preferred embodiments of the invention, the lipophilic substances are selected from hydrogenated-castor oil and glyceryl behenate.

Preferably, the lipophilic substances have an HLB value of less than 10, more preferably, less than 5.

Preferably, the lipophilic substances make up between 1% and 70% of the active layer weight, but preferably are present in a percentage between 5% and 55%, more preferably 5-35%.

The weight ratio between the content of hydrophilic polymeric substances and lipophilic substances, in the layer containing the active substance, is between 10:1 and 0.5:1 (i.e. in the range of 10:1 to 0.5:1), suitably between 10:1 and 1:1 (i.e. in the range of 10:1 to 1:1), but preferably between 7:1 and 1:1 (i.e. in the range of 7:1 to 1:1).

Besides the previously cited hydrophilic polymers and the lipophilic substances, lipophilic and/or substances of amphiphilic nature may be used in the formulation, in which the hydrophilic portion can be represented by glycerol molecules or other polyalcohols or polyethyleneglycol molecules (PEG) of molecular weight between 100 and 10,000, whereas the lipophilic part is represented by unsaturated and/or saturated fatty acids, in hydrogenated vegetable oil form. The association of the hydrophilic portion with the lipidic chain is obtained by esterification reactions or partial alcoholysis of hydrogenated vegetable oils by PEG molecules or glycerol or other polyol. In this way compounds characterised by a different degree of hydrophilicity are obtained that can be assessed by measuring the Hydrophilic-Lipophilic Balance (HLB). Triglycerides are available with an HLB value between 1 and 2, diglycerides with HLB between 2 and 3, monoglycerides with HLB between 3 and 4, PEG diesters with HLB between 6 and 15, PEG monoesters with HLB between 10 and 17. In practice, increasing the HLB values increases the hydrophilic tendency and, obviously, decreases the lipophilic tendency. Tablets according to the present invention may therefore also contain polymeric substances of a lipophilic nature.

Finally, adjuvants normally used in the pharmaceutical technique may be employed, for example, diluents, binders, lubricants, glidants and non-stick types, for example, starch, mannitol, lactose, sorbitol, xylitol, talc, stearic acid, sodium benzoate, magnesium stearate, colloidal silica, maltodextrin, and other excipients known to the expert in the field.

In order to promote the penetration of water and/or aqueous fluids in the layer or nucleus, hydrophilic diluents, for example, mannitol, lactose, starches of different origins, sorbitol, xylitol are introduced, or substances with wetting properties and/or those generally encouraging the penetration of water in the solid are preferably carried in the formulation.

Moreover, diluents, binders, lubricants, buffers, non-stick substances, glidants and plasticising substances can be employed as well as others capable of giving said layer the desired characteristic as will be better illustrated in the examples quoted later on.

Said adjuvants are preferably contained in a percentage between 5% to 50%, preferably from 10% to 40% or 20 to 50% or 20% to 35% of the weight of said active layer. The weight ratio of the active substance (i) to that of the adjuvant component (iv) in the active layer can be in the range of from 0.001:1 and 4:1, suitably of from 0.003:1 to 3:1.

The polymeric substances employed for the preparation of the barrier layer in association with other adjuvants, are able to provide a barrier (applied by compression) which proves impermeable to the carried active substance in the underlying layer for a time period that strictly depends on its composition, which can vary from 1 hour to approx. 20-24 hours or more. In such case, the release of the active substance in the stated periods (e.g. during the first hour after oral administration/immersion in aqueous fluids) occurs only from the surface of the tablet not covered by the barrier. "Impermeability" is to be construed accordingly. Preferably, during the first hour after oral administration or immersion in aqueous liquids (e.g. water), release of the active substance occurs substantially only from the surface of the tablet not covered by the barrier.

To test the impermeability of the barrier layer to the release of the active substance, various suitable tests can be conceived by persons skilled in the art of pharmaceutical tablet formulation. However, one such test may be based on selective coating of the free surfaces of the active layer with a suitable substance, such as an enteric coat (for example, "Eudragit"), or a waxy material (for example, beeswax) such that normal release of active does not occur through these surfaces. An in vitro dissolution test can then be performed in which the dissolution fluid can be sampled at appropriate time points. In this way, the point in time can be determined at which the active substance is released through the barrier layer through the interaction of the component substances of the barrier layer with the aqueous environment (that is to say the point in time at which the polymers of the barrier layer permit release). Alternatively, the free surfaces of the barrier layer(s) can be selectively coated as above and a dissolution test performed. The release profile obtained would correspond to that of an uncoated tablet up to the point in time at which the active substance was able to permeate the barrier layer and be released from the uncoated tablet.

As noted above, the barrier layer may be superposed over one or more free surfaces of the active layer in the tablet. Generally, the barrier layer will form a layer to cover one or more lateral surfaces of the active layer. In a preferred embodiment of the present invention, tablets are provided in which one or more barrier layers are used to cover one or both surfaces or bases of the active layer. Such arrangements therefore provide for a bi-layer or a tri-layer tablet.

The natural synthetic hydrophilic polymeric materials, usable in the formulation of the barrier layer, can be chosen from among those listed for the preparation of the active layer. Said polymeric substances can be present in a percentage of 5 to 90%, with respect to the total weight of said layer but, preferably, between 25% and 85%.

Said polymeric substances, utilised individually or mixed together and mixed with the lipophilic substances, are able to bring about the impermeability in the release of the carried active principle in the underlying layer for a time interval that can vary from 1 hours to approx. 20-24 hours or more, depending on the composition.

For the preparation of the barrier layer such lipophilic substances can be chosen from those listed for preparation of the active layer. Said lipophilic substances can be present in a percentage between 5% and 70% with respect to the total weight of said layer but, preferably, between 5% and 55%.

The weight ratio of hydrophobic swelling and/or gelling and/or erodible polymeric substances to lipophilic substances contained in the barrier layer can be in the range of 1:1 and 7.5:1, suitably of from 1.5:1 to 4:1, and preferably from 2:1 to 3.5:1.

Said barrier layer(s), applied by compression, can have a thickness between 0.1 and 4.5 mm. The matrix preparation can be carried out by the compression of powder or granular mixtures, for example by blending followed by dry compression or wet granulation followed by compression, and preferably working between 1000 and 5000 $Kg/cm^2$.

In general, tabletting can be through direct compression, i.e. a mixture of dry powders being compressed, but this can sometimes cause quality issues such as segregation, poor flow etc. These issues can be improved by the use of granulation techniques on all or part of the constituent mix.

Granulation is a process in which powder particles are agglomerated together to form granules. This can be carried out to:
1. improve the flow properties of a powder mixture,
2. prevent segregation of the constituent powders (improve homogeneity),
3. improve compression characteristics,
4. achieve densification of powder mixes, and/or
5. achieve alteration of particle size/shape/hydrophilic properties The tablet of the invention may be prepared by dry granulation. Dry Granulation is granulation by compression of powders by either slugging or roller compaction. It is essentially a densification process.

Slugging is where a crude compact (slug) is produced to a set weight/thickness for a given diameter of slug. These slugs are then reduced by either grating or commuting mill to produce granules of the required particle size/range.

Roller compaction or Chilsonating is where a powder mix is forced via an auger between 2 rollers (which can be smooth or grooved). Compaction of this material is controlled by the feed rate to the rollers and the hydraulic force of the rollers being pushed together. The resulting compact (called a ribbon or strip) is then reduced by either grating or commuting mill to produce granules of the required-particle size/range.

Where dry granulation is used, the adjuvants often differ slightly compared to wet granulation. For example, instead of lactose monohydrate (often used in wet granulation), one preferably uses spray-dried lactose preferably containing amorphous lactose (e.g. Fast-Flo lactose, Seppic, Paris, France).

However, the tablet of the invention is preferably prepared by wet granulation. Wet Granulation is the most widely used granulation technique, and involves powder densification and/or agglomeration by the incorporation of a granulation fluid/medium to the powder mix. Wet granulation can be aqueous-based or solvent-based, e.g. based on organic solvents. Shear is dependent on the speed of the granulator paddle/blade through the powder. Various mixer designs are available, for example:

Wet High Shear, (rotating high shear forces (Fielder))
Wet Low Shear, (rotating low shear forces (Planetar mixer))
Wet Low Shear Tumble, (spraying in to tumble mixer with/ without intensifier bar)
Extrusion, (Wet solids pushed through classified screen)
Rotary Granulators, (Spheronisation, Marumerisation— spinning disk or walls of a vessel)
Spray granulation in a fluidised Bed, or
Spray dry granulation.

For the formulation of said layer-barrier, which can be applied by compression, possible adjuvants, in particular diluents, include those traditionally used in the preparation of solid forms. For example magnesium stearate, stearic acid, sodium stearate, talc, sodium benzoate, boric acid, polyethylene glycols and/or colloidal silica can be employed.

In addition diluent, lubricating, non-stick and glidant substances and other substances may be used capable of giving said layer the desired characteristic, as will be better illustrated in the examples quoted later on. Other possible components include substances able to impart a colour to the eventual tablet layer prepared and formulated in the multilayer tablet, for example iron oxide (yellow ferric oxide).

In addition a covering could be applied to said finished tablets by a coating process and/or any other process well known to experts in the field. An example of a coating is "OPADRY OY-S-28876 WHITE". OPADRY OY-S-28876 WHITE is 63% HPMC 2910 6 cP, 7% PEG 400, 30% $TiO_2$. Red/pink (0.01-0.25%) and/or yellow (0.1 to 1.5%) colourings can also be added (iron oxides), the HPMC varying between 61-66%. An alternative blue coating uses 31-32% each of HPMC 2910 3 cP and HPMC 2910 5 cP, 8% PEG400, 23-24% $TiO_2$, 1% polysorbate, and indigotine as blue dye at 4-5%.

A colourant layer or a film of gastroresistant and enterosoluble polymeric material may also be applied to said finished tablets, so as to allow the activation of the system only after the tablet has reached the duodeno-intestinal tract. Pharmaceutical systems of the latter type can be utilised for the accomplishment of tablets specifically designed to release the active principle in the latter part of the intestinal tract i.e. at colon level. In order to attain gastroresistance, polymeric materials such as cellulose acetophthalate, cellulose acetopropionate, cellulose trimellitate, polymers and acrylic and methacrylic copolymers can be used of different molecular weights and with solubility which depends on different pH values. Said materials can be applied to the finished pharmaceutical form (active layer and the barrier layer(s)) by the classical coating process, utilising solutions in organic solvents or aqueous dispersions and spraying or fluidised bed nebulisation. Said gastro-resistant and enterosoluble materials can likewise be utilised in association with retarder polymers.

One innovative embodiment is characterised in that is possible to achieve the claimed therapeutic system by utilising the production technologies currently in use, i.e. the system may be immediately set up at industrial level.

One preferred embodiment of a tablet of the present invention comprises a tablet as previously described in which the active layer consists of components (i) to (iv) wherein the active agent is present in a weight percentage of 0.05% to 200% by weight of the active layer, the adjuvant substances are present in a weight percentage of 5% to 50% by weight of the active layer, and the weight ratio of the hydrophilic polymeric substances to the lipophilic substances is in the range of from 7:1 to 1:1.

Alternatively, the active layer consists essentially of components (i) to (iv) wherein the active agent is present in a weight percentage of 0.05% to 20% by weight of the active layer, the adjuvant substances are present in a weight percentage of 5% to 50% by weight of the active layer, and the weight ratio of the hydrophilic polymeric substances to the lipophilic substances is in the range of from 7:1 to 1:1.

In certain preferred embodiments, the hydrophilic polymeric substance may comprise hydroxypropylmethylcellulose of molecular weight 2,000 to 4,000,000, sodium carboxymethylcellulose or calcium carboxymethylcellulose.

In embodiments in which the active substance is ropinirole, the tablet may be characterised by comprising (i) ropinirole present in a weight percentage of 0.05% to 20% by weight of the active layer, (ii) the hydrophilic polymeric substance being hydroxypropylmethylcellulose, sodium carboxymethylcellulose or calcium carboxymethylcellulose. (iii) the lipophilic substance being hydrogenated castor oil or glyceryl behenate, and (iv) the adjuvant substances being present in a weight percentage of 5% to 50% by weight of the active layer, in which the weight ratio of the hydrophilic polymeric substances to the lipophilic substances being in the range of from 7:1 to 1:1.

The present invention also extends to methods of treatment comprising a tablet as herein described. According to a second aspect of the invention there is provided a method of treating a disease, the method comprising the administration of a tablet as defined herein to a patient/human in need thereof. In a preferred embodiment the disease treated is Parkinson's Disease where the active substance comprises or is ropinirole or another therapeutic agent for the treatment of this condition. According to such methods, especially with ropinirole, one or more multi-layer tablets can be administered once per day to the human need of such treatment, or a single multi-layer tablet can be administered once per day. The controlled-release ropinirole tablet of the present invention is expected to be advantageous compared to the marketed ropinirole immediate-release (IR) formulation because it should allow a more constant and/or lower systemic concentration/$c_{max}$ over a 24-hr period, avoids the necessity with the IR tablet of taking ropinirole three times a day, and should avoid some of the side-effects which are possible when IR ropinirole is administered. See especially the advantageous approx. 24 hour in vitro release shown inter alia in ropinirole Examples 13-18 hereinafter: this is near-optimal for Parkinson's disease.

The invention also provides the use of a tablet as herein defined, wherein the active substance comprises or is ropinirole, in the manufacture of a medicament for the treatment of Parkinson's disease in a human. The invention also provides such a tablet for use in the treatment of Parkinson's disease.

Preferred features for the second and subsequent aspects of the invention are as for the first aspect mutatis mutandis.

The invention will now be further described by way of reference to the following Examples and Figures which are provided for the purposes of illustration only and are not to be construed as being limiting on the invention. Reference is made to a number of Figures in which.

Figure 1:
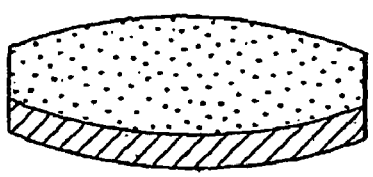
FIG. 1 shows a transverse section through a bilayer tablet in which the barrier layer is shown by hatching and the active substance containing layer by dots.
Figure 2:
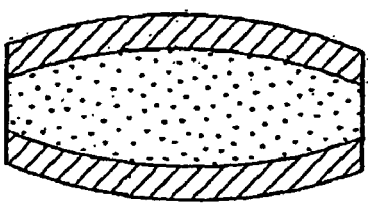
FIG. 2 shows a transverse section through a trilayer tablet which has upper and lower barrier layers and a central active layer
Figure 3:
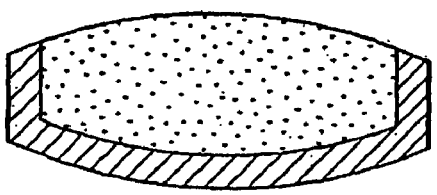
FIG. 3 shows a transverse section through a two-layer tablet, in which the barrier layer coats a lateral surface and the side of the active layer.
Figure 4:
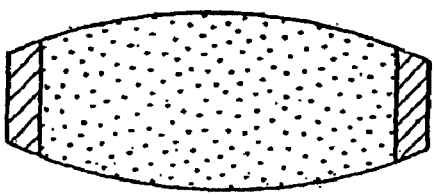
FIG. 4 shows a transverse section through a two-layer tablet in which the barrier layer is present as an annular ring around the active core.
Figure 5:
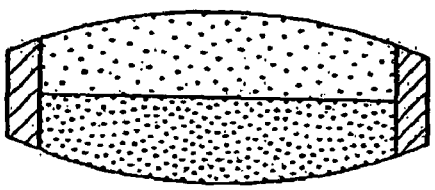
FIG. 5 shows a transverse section through a tablet of FIG. 4 in which the active core consists of two different active layers.
Figure 6:
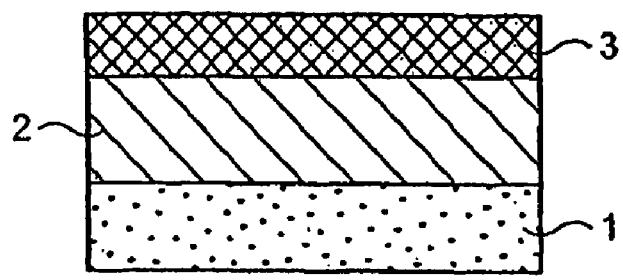
FIG. 6 shows a transverse section through a trilayer tablet in which the barrier layer (3) is superposed on active layer (2), which in turn is superposed on active layer (1).
Figure 7:
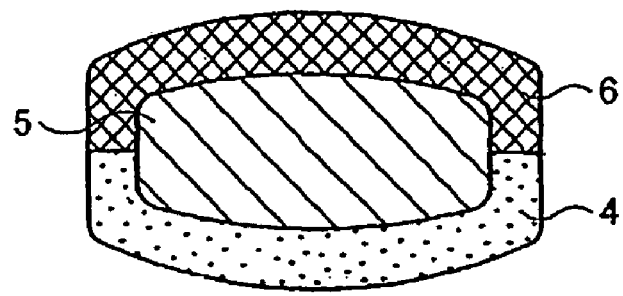
FIG. 7 shows a transverse section through a trilayer tablet in which the first active layer (5) is contained within barrier layer (6) and a second active layer (4).
Figure 8:
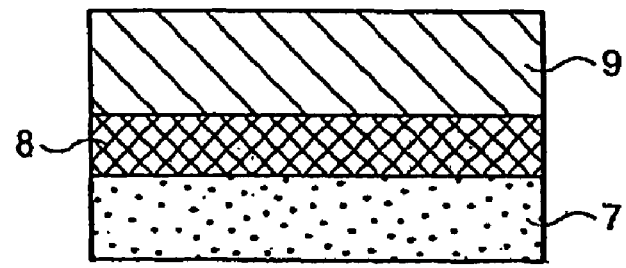
FIG. 8 shows a transverse section through a trilayer tablet in which the barrier layer (8) is present interposed between active layers (9) and (7).

FIG. 10 shows a dissolution profiles of comparison, replication batches at dosages of 0.75 mg ropinirole measured as effective free base to investigate the influence of coating on release—results shown for tablet P00K39E shown as "□", tablet P00K40E shown as "◇", tablet P00K41E shown as "Δ", tablet C511 shown as "■", tablet C519 shown as "◆", and tablet C529 shown as "▲". Results shown as percentage drug released (%) over time (hours).

FIG. 11 shows a dissolution profiles of comparison, replication batches at dosages of 6 mg ropinirole measured as effective free base to investigate the influence of coating on release—results shown for tablet P00K45E shown as "□", tablet P00K46E shown as "◇", tablet P00K47E shown as "Δ", tablet C530 shown as "■", tablet C531 shown as "◆", and tablet C532 shown as "▲". Results shown as percentage drug released (%) over time (hours).

FIG. 12 shows a dissolution profiles of comparison, replication batches at dosages of 12 mg ropinirole measured as effective free base to investigate the influence of coating on release—results shown for tablet P00K42E shown as "□", tablet P00K43E shown as "◇", tablet P00K44E shown as "Δ", tablet C512 shown as "■", tablet C534 shown as "◆", and tablet C535 shown as "▲". Results shown as percentage drug released (%) over time (hours).

FIG. 13 shows dosage influence on coated tablet displayed as a comparison of dissolution profiles of ropinirole at dosages of 0.75 mg, 6 mg and 12 mg measured as free base (results of replication batches). Results shown as percentage drug released (%) over time (hours), where tablets C511, C519 and C529 are 0.75 mg ropinirole shown as " — ", where tablets C530, C531 and C532 are 6 mg ropinirole shown as "- — - —", and where tablets C512, C534 and C535 are 12 mg ropinirole shown as " ------".

EXAMPLE 1

Systems Consisting of a Single Two-Layer Tablet—4.0 mg Pindolol

In Example 1, the first layer contains 4 mg of pindolol (slow release); the second layer consists of a "barrier" layer.
1(a) Preparation of the granulate utilised for the preparation of the layer containing 4.0 mg of slow release pinolol.

| Component | Amount (mg) |
| --- | --- |
| Pindolol | 4.0 mg |
| Mannitol (C. Erba, Milan, I) | 21.0 mg |
| Hydroxypropylmethylcellulose (HPMC) (Methocel ® K 100 M, Colorcon, Orpington, UK) | 63.0 mg (48 wt %) |
| Glyceryl behenate (Compritol 888 Gattefossé, St. Priest; F) | 35.0 mg |
| Polyvinylpyrrolidone (PVP) (Plasdone ® K29-32, I.S.P.) | 5.6 mg (4.2%) |
| Magnesium stearate (C. Erba, Milan, I) | 1.4 mg |

-continued

| Component | Amount (mg) |
|---|---|
| Colloidal silica (Syloid 244, Grace GmbH, Worms, D) | 1.4 mg |
| Total | 131.4 mg |

In total, the active layer contains 52.2 weight % of gellable, swellable and/or erodible hydrophilic polymers (PVP+ HPMC).

Mix pindolol, mannitol, hydroxypropylcellulose and glyceryl behenate, wet with an aqueous solution of 20% polyvinylpyrrolidone. Pass over a 25-mesh sieve, desiccate in a fluid-bed desiccator (Aeromatic mod. Strea) until constant weight is reached, pass over the same mesh sieve again. Add the lubricant and silica and mix in turbula for 10 minutes. In this way a granulate (granulate 1(a)) is obtained with good flow (slide) and compaction properties. The granulate is subjected to the compression stage as described later on.

1(b) Preparation of the granulate making up the second layer (barrier-layer)

| Component | Amount |
|---|---|
| Hydroxypropylmethylcellulose (Methocel ® K 100 M, Colorcon, Orpington, UK) | 45.00% |
| Glyceryl behenate (Compritol 888 Gattefossé, St. Priest; F) | 25.00% |
| Lactose monohydrate | 23.30% |
| Polyvinylpyrrolidone (Plasdone ® K29-32, I.S.P.) | 5.00% |
| Yellow iron oxide FCF aluminium lake (Colorcon, Orpington, UK) | 0.18% |
| Carmine-indigo aluminium lake 20% (Colorcon, Orpington, UK) | 0.12% |
| Magnesium stearate (USP grade, C. Erba, Milan, I) | 1.00% |
| Colloidal silica (Syloid 244, Grace GmbH, Worms, D) | 0.40% |

Mix hydroxypropylmethylcellulose, glyceryl behenate and lactose, carefully disperse the dyes. Wet with an aqueous solution of 5% polyvinylpyrrolidone. Pass over a 25-mesh sieve, desiccate in an oven (stove) at 30° C. for approximately 2 hours. Pass over the 25-mesh sieve again. Desiccate until constant weight is reached. Add the colloidal silica and magnesium stearate to the granulate obtained and mix in turbula for 15 minutes. In this way a granulate (granulate 1(b)) is obtained with good slide and compaction properties. The granulate is subjected to the compression stage as described later on.

1(c) Preparation of the Two-Layer Systems (by Compression).

The granulates, obtained as previously quoted and according to well known models to all experts in the field, are loaded in the feedboxes of a rotary compressing machine suitable for producing multi-layer tablets (e.g. Manesty Layer-Press, Liverpool, UK). In particular, the granulate described in section 1(b) is loaded in the first; whereas the granulate as described in section 1(a) is loaded in the second feedbox. The compressing machine is equipped with 9 mm diameter circular concave punches.

The machine is set so as to produce two-layer systems consisting of an initial 100 mg of granulate barrier, a second layer of 131.4 mg containing the active principle (equal to 4.0 mg of pindolol.). Working as previously described, two-layer tablets are obtained with a mean weight of 231.4 mg, each containing 4.0 mg active principle. Table 1 contains the data relating to the release verification of the active principle from the tablets in Example 1.

EXAMPLE 2

Systems Consisting of a Single Two-Layer Tablet—8.0 mg Pindolol

In Example 2, the first layer (slow release) contains 8 mg of pindolol; the second layer consists of a "barrier" layer.

A granulate is prepared as described in Example 1, in section 1(a), the only alteration being to double the amount of carried active principle. The second layer (barrier) is kept identical both qualitatively and quantitatively, as described in Example 1 in section 1(b). Working as described in section 1(c), two-layer tablets are prepared consisting of an initial amount of 100 mg of granulate barrier (barrier), a second layer of 135.4 mg containing the active principle (equal to 8.0 mg of pindolol). Hence two-layer tablets are obtained with a mean weight of 235.4 mg, each containing 8.0 mg of active principle. Table 1 contains the data relating to the release verification of the active principle from the tablets in Example 2.

EXAMPLE 3

Systems Consisting of a Single Two-Layer Tablet—16.0 mg Pindolol

In Example 3, the two-layer tablet system is as described in Examples 1 and 2 but containing 16.0 mg of pindolol.

A granulate is prepared as described in Example 1, in section 1(a), the only alteration being to carry 16 mg of active principle thus 143.4 mg of granulate contain 16.0 mg of pindolol. The second layer (barrier) is kept identical both qualitatively and quantitatively, as described in Example 1 in section 1(b). Working as described in section 1(c), two-layer tablets are prepared consisting of an initial amount of 100 mg of granulate barrier, a second layer of 143.4 mg containing the active principle (equal to 16.0 mg of pindolol). Hence two-layer tablets are obtained with a mean weight of 243.4 mg, each containing 16.0 mg of active principle. Table 1 contains the data relating to the release verification of the active principle from the tablets in Example 3.

EXAMPLE 4

Systems Consisting of a Single Two-Layer Tablet—24 mg Pindolol

In Example 4, the two-layer tablet system is as described in Examples 1 and 2 but containing 24.0 mg of pindolol.

A granulate is prepared as described in Example 1, in section 1(a), the only alteration being to carry 24 mg of active principle; thus 151.4 mg of granulate contain 24.0 mg of pindolol. The second layer (barrier) is kept identical both qualitatively and quantitatively, as described in Example 1 in section 1(b). Working as described in section 1(c), two-layer tablets are prepared consisting of an initial amount of 100 mg of granulate barrier, a second layer of 151.4 mg containing the active principle (equal to 24.0 mg of pindolol). Hence two-layer tablets are obtained with a mean weight of 251.4 mg, each containing 24.0 mg of active principle. Table 1 contains the data relating to the release verification of the active principle from the tablets in Example 4.

EXAMPLE 5

Systems Consisting of a Single Two-Layer Tablet—32.0 mg Pindolol

In Example 5, the two-layer tablet is as described in Examples 1 and 2 but containing 32.0 mg of pindolol.

A granulate is prepared as described in Example 1, in section 1(a), the only alteration being to carry 32.0 mg of active principle; thus 159.4 mg of granulate contain 32.0 mg of pindolol and 43 weight % of total gellable, swellable and/or erodible hydrophilic polymers (PVP+HPMC) or 40 wt % (more exactly 39.5 wt %) HPMC.

The second layer (barrier) is kept identical both qualitatively and quantitatively, as described in Example 1 in section 1(b). Working as described in section 1(c), two-layer tablets are prepared consisting of an initial amount of 100 mg of granulate barrier, a second layer of 159.4 mg containing the active principle (equal to 32.0 mg of pindolol). Hence two-layer tablets are obtained with a mean weight of 259.4 mg, each containing 32.0 mg of active principle. Table 1 contains the data relating to the release verification of the active principle from the tablets in Example 5.

Dissolution Test of Tablets Prepared in Examples 1 to 5

To assess the release characteristics of the active principle from the two-layer tablets, quoted in Examples 1-5, equipment 2 is utilised, paddle (USP XXIII), working at 100 r.p.m. and utilising as dissolution fluid 900 mL of 0.1M hydrochloric acid at 37° C. The release of the active principle is followed by HPLC assessment at 227 nm utilising an automatic sampling and reading system. The results of the experiments carried out are quoted in Table 1

TABLE 1

| TIME | Percentage Released | | | | |
|---|---|---|---|---|---|
| (hours) | Example 1 | Example 2 | Example 3 | Example 4 | Example 5 |
| 1 | 22.2 | 19.4 | 22.4 | 23.3 | 23.8 |
| 2 | 34.0 | 32.2 | 33.2 | 34.2 | 34.5 |
| 4 | 50.2 | 48.7 | 49.7 | 52.2 | 51.7 |
| 6 | 63.5 | 61.5 | 63.0 | 64.1 | 64.0 |
| 8 | 72.7 | 72.1 | 73.4 | 74.9 | 74.2 |
| 10 | 82.8 | 81.6 | 81.9 | 83.5 | 82.9 |
| 12 | 88.7 | 87.4 | 88.2 | 90.7 | 89.8 |
| 16 | 96.3 | 95.0 | 95.9 | 96.6 | 97.1 |
| 20 | 100.3 | 99.2 | 98.9 | 100.8 | 100.1 |

It is possible to point out that the release of the drug from the prepared systems is slowed down and the release of the whole drug takes approximately 20 hours. In addition, it is clear that the release kinetics are not substantially modified at any content level of active substance in the tablets. Such behaviour is in accordance with the present invention.

EXAMPLE 6

Systems Consisting of a Three-Layer Tablet—4 mg Molsidomine

In Example 6, a three-layer tablet is prepared in which the first layer consists of 80 mg of a "barrier" layer, the second layer (slow release) contains 4 mg of molsidomine; the third layer consists of 100 mg of a "barrier layer".

6(a) Preparation of the granulate utilised for the preparation of the layer containing 4.0 mg of slow release molsidomine.

| Component | Amount (mg) |
|---|---|
| Molsidomine | 4.00 mg |
| Mannitol (C Erba, Milan, I) | 5.00 mg |
| Hydroxypropylmethylcellulose (Methocel ® K 100 M, Colorcon, Orpington, UK) | 60.00 mg (63 wt %) |

-continued

| Component | Amount (mg) |
|---|---|
| Glyceryl behenate (Compritol 888 Gattefossé, St. Priest; F) | 20.00 mg |
| Polyvinylpyrrolidone (Plasdone ® K29-32, I.S.P.) | 3.70 mg |
| Magnesium stearate (USP grade, C. Erba, Milan, I) | 1.00 mg |
| Colloidal silica (Syloid 244, Grace GmbH, Worms, D) | 1.63 mg |
| Total | 95.33 mg |

In total, the active layer contains 66.8 weight % (i.e. 67 wt %) of gellable, swellable and/or erodible hydrophilic polymers (PVP+HPMC).

Mix molsidomine, mannitol, hydroxypropylcellulose and glyceryl behenate, wet with a 20% solution of polyvinylpyrrolidone. Pass over a 25-mesh sieve, desiccate in a fluid-bed desiccator (Aeromatic mod. Strea) until constant weight is reached, pass over the same mesh sieve again. Add the silica and mix in a cubic mixer for 45 minutes, then add the magnesium stearate and mix for a further 15 minutes. In this way a granulate (granulate 6(a)) with good slide and compaction properties. The granulate is subjected to the compression stage as described later on.

6(b) Preparation of the granulate making up the barrier-layers.

| Component | Amount |
|---|---|
| Hydroxypropylmethylcellulose (Methocel ® K 100 M, Colorcon, Orpington, UK) | 39.88% |
| Glyceryl behenate (Compritol 888 Gattefossé, St. Priest; F) | 13.50% |
| Lactose monohydrate | 39.88% |
| Polyvinylpyrrolidone (Plasdone ® K29-32, I.S.P.) | 5.00% |
| Yellow iron oxide FCF (Sicovit Gelb 10-BASF Koln; D) | 0.24% |
| Magnesium stearate (USP grade, C. Erba, Milan, I) | 1.00% |
| Colloidal silica (Syloid 244, Grace GmbH, Worms, D) | 0.50% |
| Total | 100% |

Mix hydroxypropylmethylcellulose, glyceryl behenate and lactose, carefully disperse the dye. Wet with a 5% aqueous solution of polyvinylpyrrolidone. Pass over a 25-mesh sieve, desiccate in an oven (stove) at 30° C. for approximately 2 hours. Pass over a 25-mesh sieve again. Desiccate until constant weight is reached. Add the colloidal silica and magnesium stearate to the granulate obtained and mix in turbula for 15 minutes. In this way a granulate (granulate 6(b)) is obtained with good slide and compaction properties. The granulate is subjected to the compression stage as described later on.

6(c) Preparation of the Three-Layer Systems (by Compression).

The granulates, obtained as previously quoted and according to well known models to all experts in the field, are loaded in the feedboxes of a rotary compressing machine suitable for producing three-layer tablets (e.g. Manesty Layer-Press LP 39, Liverpool, UK). In particular, the granulate described in section 6(b) is loaded in the first and third feedboxes; whereas the granulate as described in section 6(a) is loaded in the second feedbox. The compressing machine is equipped with 8 mm diameter circular concave punches.

The machine is set so as to produce three-layer systems consisting of an initial 80.0 mg of granulate barrier, a second layer of 95.33 mg containing the active principle (equal to 4.0 mg of molsidomine) and a third layer of 100.0 mg of granulate barrier. Working as previously described, three-layer tablets are obtained with a mean weight of 275.33 mg, each containing 4.0 mg active principle. Table 2 contains the data relating to the release verification of the active principle from the tablets in Example 6.

EXAMPLE 7

Systems Consisting of a Single Three-Layer Tablet—8 mg Molsidomine

In Example 7, the first layer consists of 80 mg of a "barrier" layer, the second layer (slow release) contains 8 mg of molsidomine; the third layer consists of 100 mg of a "barrier" layer.

A granulate is prepared as described in Example 6, in section 6(a), the only alteration being to double the amount of carried active principle; such a granulate makes up the second layer of the three layer tablet. For the first and third layer (barrier) a qualitatively and quantitatively identical granulate is employed, as described in Example 6 in section 6(b). The compressing machine is equipped with 8 mm diameter circular concave punches.

The machine is set so as to produce three-layer systems consisting of an initial 80.0 mg of granulate barrier, a second layer of 99.33 mg containing the active principle (equal to 8.0 mg of molsidomine) and a third layer of 100.0 mg of granulate barrier. Working as previously described, three-layer tablets are obtained with a mean weight of 279.33 mg, each containing 8.0 mg of active principle. Table 2 contains the data relating to the release verification of the active principle from the tablets in Example 7.

EXAMPLE 8

Systems Consisting of a Single Three-Layer Tablet—16 mg Molsidomine

In Example 8, the first layer consists of 80 mg of a "barrier" layer, the second layer (slow release) contains 16 mg of molsidomine; the third layer consists of 100 mg of a "barrier" layer. A granulate is prepared as described in Example 6, in section 6(a), the only alteration being to double the amount of carried active principle; such a granulate makes up the second layer of the three layer tablet.

For the first and third layer (barrier) a qualitatively and quantitatively identical granulate is employed, as described in Example 6 in section 6(b). The compressing machine is equipped with 8 mm diameter circular concave punches. The machine is set so as to produce three-layer systems consisting of an initial 80.0 mg of granulate barrier, a second layer of 107.33 mg containing the active principle (equal to 16.0 mg of molsidomine) and a third layer of 100.0 mg of granulate barrier. Working as previously described, three-layer tablets are obtained with a mean weight of 287.33 mg, each containing 16.0 mg of active principle. Table 2 contains the data relating to the release verification of the active principle from the tablets in Example 8.

EXAMPLE 9

Systems Consisting of a Single Three-Layer Tablet—20 mg Molsidomine

In Example 9, the first layer consists of 80 mg of a "barrier" layer, the second layer (slow release) contains 20 mg of molsidomine; the third layer consists of 100 mg of a "barrier" layer. A granulate is prepared as described in Example 6, in section 6(a), the only alteration being to double the amount of carried active principle; such a granulate makes up the second layer of the three layer tablet. For the first and third layer (barrier) a qualitatively and quantitatively identical granulate is employed, as described in Example 6 in section 6(b). The compressing machine is equipped with 8 mm diameter circular concave punches.

The machine is set so as to produce three-layer systems consisting of an initial 80.0 mg of granulate barrier, a second layer of 111.33 mg containing the active principle (equal to 20.0 mg of molsidomine) and 57.2 weight % of gellable, swellable and/or erodible hydrophilic polymers (PVP+HPMC) or 54 wt % HPMC, and a third layer of 100.0 mg of granulate barrier. Working as previously described, three-layer tablets are obtained with a mean weight of 291.33 mg, each containing 20.0 mg of active principle. Table 2 contains the data relating to the release verification of the active principle from the tablets in Example 9.

Dissolution Test of Tablets Prepared in Examples 6 to 9

To assess the release characteristics of the active principle from the three-layer tablets, quoted in Examples 6 to 9, equipment 2 is utilised, paddle (USP XXIII), working at 100 r.p.m. and utilising as dissolution fluid 900 mL of distilled water at 37° C. The release of the active principle is followed by U.V. spectrophotometric assessment at 311 nm utilising an automatic sampling and reading system. The results of the experiments carried out are quoted in Table 2

TABLE 2

| TIME | Percentage Released | | | |
|---|---|---|---|---|
| (hours) | Example 6 | Example 7 | Example 8 | Example 9 |
| 1 | 12.3 | 11.4 | 11.9 | 12.6 |
| 2 | 19.6 | 20.7 | 18.8 | 21.2 |
| 4 | 32.7 | 33.8 | 31.5 | 33.0 |
| 6 | 41.5 | 43.0 | 42.5 | 43.1 |
| 8 | 52.8 | 54.2 | 53.0 | 54.5 |
| 10 | 64.0 | 66.5 | 65.3 | 63.6 |
| 12 | 74.7 | 76.4 | 75.2 | 77.0 |
| 16 | 88.4 | 89.6 | 86.8 | 89.8 |
| 20 | 96.5 | 98.0 | 95.9 | 96.6 |
| 24 | 100.3 | 102.3 | 99.4 | 101.8 |

It is possible to point out that the release of the drug from the prepared systems is slowed down and the release of the whole drug takes approximately 20 hours. In addition, it is clear that the release kinetics are not substantially modified at any content level of active substance in the tablets. Such behaviour is in accordance with the present invention.

EXAMPLE 10

Systems Consisting of a Single Three-Layer Tablet—0.1 mg of Moxonidina

In Example 10, the first layer consists of 100 mg of a "barrier" layer, the second layer (slow release) contains 0.1 mg of moxonidina; the third layer consists of 100 mg of a "barrier" layer.

10(a) Preparation of the granulate utilised for the preparation of the layer containing 0.1 mg of slow release moxonidina.

| Component | Amount (mg) |
| --- | --- |
| Moxonidina | 0.10 mg |
| Lactose monohydrate | 29.90 mg |
| Hydroxypropylmethylcellulose (Methocel ® K 100 M, Colorcon, Orpington, UK) | 50.00 mg (52 wt %) |
| Glyceryl behenate (Compritol 888 Gattefossé, St. Priest; F) | 10.00 mg |
| Polyvinylpyrrolidone (Plasdone ® K29-32, I.S.P.) | 5.00 mg |
| Magnesium stearate (USP grade, C. Erba, Milan, I) | 1.00 mg |
| Colloidal silica (Syloid 244, Grace GmbH, Worms, D) | 1.00 mg |
| Total | 97.00 mg |

In total, the active layer contains 56.7 weight % of gellable, swellable and/or erodible hydrophilic polymers (PVP+HPMC).

Mix moxonidina, lactose, hydroxypropylcellulose and glyceryl behenate, wet with a solution of 20% polyvinylpyrrolidone. Pass over a 25-mesh sieve, desiccate in a fluid-bed desiccator (Aeromatic mod. Strea) until constant weight is reached, pass over the same mesh sieve again. Add the silica and mix in a cubic mixer for 45 minutes, then add the magnesium stearate and mix for a further 15 minutes. In this way a granulate granulate 10(a)) is obtained with good slide and compaction properties. The granulate is subjected to the compression stage as described later on.

10(b) Preparation of the granulate making up the barrier-layers.

The composition and granulate described in Example 6(b) is utilised.

| Component | Amount |
| --- | --- |
| Hydroxypropylmethylcellulose (Methocel ® K 100 M, Colorcon, Orpington, UK) | 39.88% |
| Glyceryl behenate (Compritol 888 Gattefossé, St. Priest; F) | 13.50% |
| Lactose monohydrate | 39.88% |
| Polyvinylpyrrolidone (Plasdone ® K29-32, I.S.P.) | 5.00% |
| Yellow iron oxide FCF (Sicovit Gelb 10-BASF Koln; D) | 0.24% |
| Magnesium stearate (USP grade, C. Erba, Milan, I) | 1.00% |
| Colloidal silica (Syloid 244, Grace GmbH, Worms, D) | 0.50% |
| Total | 100.00% |

Mix hydroxypropylmethylcellulose, glyceryl behenate and lactose and carefully disperse the dye. Wet with a 5% an aqueous solution of polyvinylpyrrolidone. Pass over a 25-mesh sieve, desiccate in an oven (stove) at 30° C. for approximately 2 hours. Pass over the 25-mesh sieve again. Desiccate until constant weight is reached. Add the colloidal silica and magnesium stearate to the granulate obtained and mix in turbula for 15 minutes. In this way a granulate (granulate 10(b)) is obtained with good slide and compaction properties. The granulate is subjected to the compression stage as described later on.

10(c) Preparation of the Three-Layer Systems (by Compression).

The granulates obtained as previously quoted and according to well known models to all experts in the field, are loaded in the feedboxes of a rotary compressing machine suitable for producing three-layer tablets (e.g. Manesty Layer-Press LP 39, Liverpool, UK). In particular, the granulate described in section 10(b) is loaded in the first and third feedboxes; whereas the granulate as described in section 10(a) is loaded in the second feedbox. The compressing machine is equipped with 9 mm diameter circular concave punches. The machine is set so as to produce three-layer systems consisting of an initial 100.00 mg of granulate barrier, a second layer of 97.00 mg containing the active principle (equal to 0.10 mg of moxonidina.) and a third layer of 100.0 mg of granulate barrier. Working as previously described, three-layer tablets are obtained with a mean weight of 297.00 mg, each containing 0.1 mg of active principle. Table 3 contains the data relating to the release verification of the active principle from the tablets in Example 10.

EXAMPLE 11

Systems Consisting of a Single Three-Layer Tablet—0.30 mg Moxonidina

In Example 11, the first layer consists of 100 mg of a "barrier" layer, the second layer (slow release) of 97.00 mg containing the active principle (equal to 0.30 mg of moxonidina); the third layer consists of 100 mg of a "barrier" layer.

11(a) Preparation of the granulate utilised for the preparation of the layer containing 0.3 mg of slow release moxonidina.

| Component | Amount (mg) |
| --- | --- |
| Moxonidina | 0.30 mg |
| Lactose monohydrate | 29.70 mg |
| Hydroxypropylmethylcellulose (Methocel ® K 100 M, Colorcon, Orpington, UK) | 50.00 mg |
| Glyceryl behenate (Compritol 888 Gattefossé, St. Priest; F) | 10.00 mg |
| Polyvinylpyrrolidone (Plasdone ® K29-32, I.S.P.) | 5.00 mg |
| Magnesium stearate (USP grade, C. Erba, Milan, I) | 1.00 mg |
| Colloidal silica (Syloid 244, Grace GmbH, Worms, D) | 1.00 mg |
| Total | 97.00 mg |

A granulate is prepared as described in Example 10, in section 10(a), the only alteration being to triple the amount of carried active principle; such a granulate makes up the second layer of the three-layer tablet.

For the first and third layer (barrier) a qualitatively and quantitatively identical granulate is employed, as described in Example 6 in section 6(b). The compressing machine is equipped with 9.0 mm diameter circular concave punches. The machine is set so as to produce three-layer systems consisting of an initial 100.0 mg of granulate barrier, a second layer of 97.00 mg containing the active principle (equal to 0.3 mg of moxonidina) and a third layer of 100.0 mg of granulate barrier. Working as previously described, three-layer tablets are obtained with a mean weight of 297.00 mg, each containing 0.3 mg of active principle. Table 3 contains the data relating to the release verification of the active principle from the tablets in Example 1.

EXAMPLE 12

Systems Consisting of a Single Three-Layer Tablet—1.2 mg Moxonidina

In Example 12, the first layer consists of 100 mg of a "barrier" layer, the second layer (slow release) of contains 1.2 mg of moxonidina; the third layer consists of 100 mg of a "barrier" layer.

12(a) Preparation of the granulate utilised for the preparation of the layer containing 1.2 mg of slow release moxonidina.

| Component | Amount (mg) |
| --- | --- |
| Moxonidina | 1.20 mg |
| Lactose monohydrate | 28.80 mg |
| Hydroxypropylmethylcellulose (Methocel ® K 100 M, Colorcon, Orpington, UK) | 50.00 mg (52 wt %) |
| Glyceryl behenate (Compritol 888 Gattefossé, St. Priest; F) | 10.00 mg |
| Polyvinylpyrrolidone (Plasdone ® K29-32, I.S.P.) | 5.00 mg |
| Magnesium stearate (USP grade, C. Erba, Milan, I) | 1.00 mg |
| Colloidal silica (Syloid 244, Grace GmbH, Worms, D) | 1.00 mg |
| Total | 97.00 mg |

In total, the active layer contains 56.7 weight % of gellable, swellable and/or erodible hydrophilic polymers (PVP+HPMC).

A granulate is prepared as described in Example 11, in section 11(a), the only alteration being to quadruple the amount of carried active principle; such a granulate makes up the second layer of the three-layer tablet.

For the first and third layer (barrier) a qualitatively and quantitatively identical granulate is employed, as described in Example 6 in section 6(b). The compressing machine is equipped with 9.0 mm diameter circular concave punches. The machine is set so as to produce three-layer systems consisting of an initial 100.0 mg of granulate barrier, a second layer of 97.00 mg containing the active principle (equal to 1.20 mg of moxonidina) and a third layer of 100.0 mg of granulate barrier. Working as previously described, three-layer tablets are obtained with a mean weight of 297.00 mg, each containing 1.20 mg of active principle. Table 3 contains the data relating to the release verification of the active principle from the tablets in Example 12.

Dissolution Test of Tablets Prepared in Examples 10 to 12

To assess the release characteristics of the active principle from the three-layer tablets, quoted in Examples 10-12, equipment 2 is utilised, paddle (USP XXIII), working at 100 r.p.m. and utilising as dissolution fluid 900 mL of distilled water at 37° C. The release of the active principle is followed by HPLC assessment at 230 nm utilising an automatic Hewlett-Packard system with a diode array detector. The results of the experiments carried out are quoted in Table 3.

TABLE 3

| TIME | Percentage Released | | |
| --- | --- | --- | --- |
| (hours) | Example 10 | Example 11 | Example 12 |
| 1 | 12.4 | 12.7 | 14.7 |
| 2 | 20.1 | 21.8 | 23.1 |
| 4 | 35.3 | 35.9 | 37.8 |
| 6 | 50.0 | 52.1 | 54.3 |
| 8 | 62.6 | 63.8 | 64.7 |
| 10 | 75.8 | 77.1 | 78.0 |
| 12 | 85.8 | 87.4 | 88.6 |
| 16 | 98.7 | 99.1 | 98.9 |
| 20 | 100.3 | 101.2 | 99.4 |

It is possible to point out that the release of the drug from the prepared systems is slowed down and the release of the whole drug takes approximately 20 hours. In addition, it is clear that the release kinetics are not substantially modified, even if the active substance content in the tablets varies by 120%. Such behaviour is in accordance with the present invention.

EXAMPLE 13

Systems Consisting of a Single Three-Layer Tablet—0.75 mg Ropinirole

In Example 13, the first layer consists of 130 mg of a "barrier" layer, the second layer (slow release) contains 0.86 mg of Ropinirole HCl equal to 0.75 mg of base; the third layer consists of 120 mg of a "barrier" layer.

13(a) Preparation of the granulate utilised for the preparation of the slow release base layer containing 0.86 mg of Ropinirole HCl equal to 0.75 mg of base.

| Component | Amount (mg) |
| --- | --- |
| Ropinirole HCl equal to 0.75 mg of base | 0.86 mg |
| Hydroxypropylmethylcellulose (HPMC) (Methocel ® K 100 M, Colorcon, Orpington, UK) | 61.50 mg (41 wt %) |
| Sodium carboxymethylcellulose (NaCMC) (Blanose 9 M31XF) | 15.00 mg (10 wt %) |
| Maltodextrin NF (Lycatab DSH) | 7.50 mg (5 wt %) |
| Lactose (C. Erba, Milan, I) | 47.74 mg |
| Hydrogenated castor oil (Cutina HR-Henkel, D) | 15.00 mg (10 wt %) |
| Magnesium stearate (C. Erba, Milan, I) | 1.50 mg (1 wt %) |
| Colloidal silica (Syloid 244, Grace GmbH, Worms, D) | 0.90 mg |
| Total | 150.00 mg |

In total, the active layer contains 51 weight % of the gellable, swellable and/or erodible hydrophilic polymers (HPMC+NaCMC), or 56 wt % if one includes maltodextrin.

Mix the Ropinirole and a part of the lactose for 20 minutes in a suitable mixer-granulator, (type Niro-Fielder PMA). Add the hydroxypropymethylcellulose, sodium carboxymethylcellulose, hydrogenated castor oil, maltodextrin and the remainder of the lactose and mix for 10 minutes, wet with water (approx. 30% of the weight of the products utilised). The granulate obtained is desiccated in a fluid-bed desiccator (type Niro-Fielder TSG 2) until constant weight is reached. Pass over an 0.800 mm mesh sieve oscillating granulator again. Add the silica and mix in a cubic mixer for 20 minutes, then add the magnesium stearate and mix for a further 10 minutes. In this way a granulate (granulate 13(a)) is obtained with good slide and compaction properties. The granulate is subjected to the compression stage as described later on.

13(b) Preparation of the granulate making up the barrier-layers.

| Component | Amount |
| --- | --- |
| Hydroxypropylmethylcellulose (Methocel ® K 100 M, Colorcon, Orpington, UK) | 44.76% (or 44.75%) |
| Mannitol (C. Erba) | 23.60% |
| Glyceryl behenate (Compritol 888 Gattefossé, St. Priest; F) | 25.00% |
| Polyvinylpyrrolidone (PVP) (Plasdone ® K29-32, I.S.P.) | 5.00% |
| Yellow iron oxide FCF (Sicovit Gelb 10-BASF Koln; D) | 0.24% (or 0.25%) |

-continued

| Component | Amount |
|---|---|
| Magnesium stearate (USP grade, C. Erba, Milan, I) | 1.00% |
| Colloidal silica (Syloid 244, Grace GmbH, Worms, D) | 0.40% |
| Total | 100.00% |

Mix hydroxypropylmethylcellulose, glyceryl behenate and mannitol and carefully disperse the dye. Wet with a 5% aqueous solution of polyvinylpyrrolidone. Pass over a 25-mesh sieve, desiccate in an oven (stove) at 30° C. for approximately 2 hours. Pass over the 25-mesh sieve again. Desiccate until constant weight is reached. Add the colloidal silica and magnesium stearate to the granulate obtained and mix in turbula for 15 minutes. In this way a granulate (granulate 13(b)) is obtained with good slide and compaction properties. The granulate is subjected to the compression stage as described later on.

13(c) Preparation of the Three-Aver Systems (by Compression).

The granulates, obtained as previously quoted and according to well known models to all experts in the field, are loaded in the feedboxes of a rotary compressing machine suitable for producing three-layer tablets (e.g. Manesty Layer-Press LP 39, Liverpool, UK). In particular, the granulate described in section 13(b) is loaded in the first and third feedboxes; whereas the granulate as described in section 13(a) is loaded in the second feedbox. The compressing machine is equipped with a slightly concave 9 mm diameter circular punches.

The machine is set so as to produce three-layer systems consisting of an initial 130.0 mg of granulate barrier, a second layer of 150 mg containing the active principle (0.86 mg of Ropinirole HCl equal to 0.75 mg of base) and a third layer of 120.0 mg of granulate barrier. Working as previously described, three-layer tablets are obtained with a mean weight of 400.00 mg, each containing 0.86 mg of Ropinirole HCl, each equal to 0.75 mg of base. Table 4 contains the data relating to the release verification of the active principle from the tablets in Example 13.

EXAMPLE 13A

Variation of Example 13

In an alternative embodiment to Example 13, the preparation of the granulate for the active layer 13(a) is done as follows:

Mix the HPMC, ropinirole, lactose, Na CMC, hydrogenated castor oil and maltodextrin for 6 minutes in a suitable mixer-granulator (type Niro Fielder PMA). Wet with water (approx. 30% of the weight of the products utilised). The granule obtained is desiccated in a fluid bed dryer (type Niro Fielder TSG 2) until the water content is between 1 and 4.5%. Pass through a 1.57 mm mesh sieve in a cone mill. Add silica and mix in a cubic mixer for 20 minutes, then add the magnesium stearate and mix for a further 2 minutes.

In this alternative embodiment, the preparation of the granulate for the barrier layer 13(b) is done as follows:

Mix the mannitol, the dye, the glyceryl behenate, the HPMC, and the PVP for 6 minutes in a suitable mixer-granulator (type Niro Fielder PMA). Wet with water (approx. 25% of the weight of the products utilised). The granule obtained is desiccated in a fluid bed dryer (type Niro Fielder TSG 2) until water content is between 1.1 and 2.7%. Pass through a 1.57 mm mesh sieve in a cone mill. Add silica and mix in a cubic mixer for 20 minutes, then add the magnesium stearate and mix for a further 2 minutes.

In further alternative embodiments, the above alternative procedures can also be used, mutatis mutandis, with the ingredients/formulations of any of the Examples 14 to 23 hereinafter.

EXAMPLE 14

Systems Consisting of a Single Three-Layer Tablet—1.00 mg Ropinirole

In Example 14, the first layer consists of 130 mg of a "barrier" layer, the second layer (slow release) contains 1.14 mg of Ropinirole HCl equal to 1.00 mg of base; the third layer consists of 120 mg of a "barrier" layer.

A granulate is prepared as described in Example 13, in section 13(a), the only alteration being to increase the amount of carried active principle, reducing the lactose content by the same amount; such granulate makes up the second layer of the three-layer tablet.

14(a) Preparation of the granulate utilised for the preparation of the slow release layer containing 1.14 mg of Ropinirole HCl equal to 1.00 mg of base.

| Component | Amount (mg) |
|---|---|
| Ropinirole HCl equal to 1.00 mg of base | 1.14 mg |
| Hydroxypropylmethylcellulose (Methocel ® K 100 M, Colorcon, Orpington, UK) | 61.50 mg |
| Sodium carboxymethylcellulose (Blanose 9 M31XF) | 15.00 mg |
| Maltodextrin NF (Lycatab DSH) | 7.50 mg |
| Lactose (C. Erba, Milan, I) | 47.46 mg |
| Hydrogenated castor oil (Cutina HR-Henkel, D) | 15.00 mg |
| Magnesium stearate (C. Erba, Milan, I) | 1.50 mg |
| Colloidal silica (Syloid 244, Grace GmbH, Worms, D) | 0.90 mg |
| Total | 150.00 mg |

For the first and third layer (barrier) a qualitatively and quantitatively identical granulate is employed, as described in Example 13 in section 13(b). The compressing machine is equipped with slightly concave 9 mm diameter circular punches.

The machine is set so as to produce three-layer systems consisting of an initial 130.0 mg of granulate barrier, a second layer of 150 mg containing 1.14 mg of Ropinirole HCl (equal to 1.00 mg of Ropinirole base) and a third layer of 120.0 mg of granulate barrier. Working as previously described, three-layer tablets are obtained with a mean weight of 400.00 mg, each containing 1.14 mg of Ropinirole HCl, equal to 1.00 mg of base. Table 4 contains the data relating to the release verification of the active principle from the tablets in Example 14.

EXAMPLE 15

Systems Consisting of a Single Three-Layer Tablet—3.00 mg Ropinirole

In Example 15, the first layer consists of 130 mg of a "barrier" layer, the second layer (slow release) contains 3.42 mg of Ropinirole HCl equal to 3.00 mg of base; the third layer consists of 120 mg of "barrier" layer.

A granulate is prepared as described in Example 13, in section 13(a), the only alteration being to increase the amount of carried active principle, reducing the lactose content by the same amount; such granulate makes up the second layer of the three-layer tablet.

15(a) Preparation of the granulate utilised for the preparation of the slow release layer containing 3.42 mg of Ropinirole HCl equal to 3.00 mg of base.

| Component | Amount (mg) |
|---|---|
| Ropinirole HCl equal to 3.00 mg of base | 3.42 mg |
| Hydroxypropylmethylcellulose (Methocel ® K 100 M, Colorcon, Orpington, UK) | 61.50 mg |
| Sodium carboxymethylcellulose (Blanose 9 M31XF) | 15.00 mg |
| Maltodextrin NF (Lycatab DSH) | 7.50 mg |
| Lactose (C. Erba, Milan, I) | 45.18 mg |
| Hydrogenated castor oil (Cutina HR-Henkel, D) | 15.00 mg |
| Magnesium stearate (C. Erba, Milan, I) | 1.50 mg |
| Colloidal silica (Syloid 244, Grace GmbH, Worms, D) | 0.90 mg |
| Total | 150.00 mg |

For the first and third layer (barrier) a qualitatively and quantitatively identical granulate is employed, as described in Example 13 in section 13(b). The compressing machine is equipped with slightly concave 9 mm diameter circular punches.

The machine is set so as to produce three-layer systems consisting of an initial 130.0 mg of granulate barrier, a second layer of 150 mg containing 3.42 mg of Ropinirole HCl (equal to 3.00 mg of Ropinirole base) and a third layer of 120.0 mg of granulate barrier. Working as previously described, three-layer tablets are obtained with a mean weight of 400.00 mg, each containing 3.42 mg of Ropinirole HCl, each equal to 3.00 mg of base. Table 4 contains the data relating to the release verification of the active principle from the tablets in Example 15.

EXAMPLE 16

Systems Consisting of a Single Three-Layer Tablet—6.00 mg Ropinirole

In Example 16, the first layer consists of 130 mg of a "barrier" layer, the second layer (slow release) contains 6.84 mg of Ropinirole HCl equal to 6.00 mg of base; the third layer consists of 120 mg of a "barrier" layer.

A granulate is prepared as described in Example 13, in section 13(a), the only alteration being to increase the amount of carried active principle, reducing the lactose content by the same amount; such granulate makes up the second layer of the three-layer tablet.

16(a) Preparation of the granulate utilised for the preparation of the slow release layer containing 6.84 mg of Ropinirole HCl equal to 6.00 mg of base.

| Component | Amount (mg) |
|---|---|
| Ropinirole HCl equal to 6.00 mg of base | 6.84 mg |
| Hydroxypropylmethylcellulose (Methocel ® K 100 M, Colorcon, Orpington, UK) | 61.50 mg |
| Sodium carboxymethylcellulose (Blanose 9 M31XF) | 15.00 mg |
| Maltodextrin NF (Lycatab DSH) | 7.50 mg |
| Lactose (C. Erba, Milan, I) | 41.76 mg |
| Hydrogenated castor oil (Cutina HR-Henkel, D) | 15.00 mg |
| Magnesium stearate (C. Erba, Milan, I) | 1.50 mg |
| Colloidal silica (Syloid 244, Grace GmbH, Worms, D) | 0.90 mg |
| Total | 150.00 mg |

For the first and third layer (barrier) a qualitatively and quantitatively identical granulate is employed, as described in Example 13 in section 13(b). The compressing machine is equipped with slightly concave 9 mm diameter circular punches. The machine is set so as to produce three-layer systems consisting of an initial 130.0 mg of granulate barrier, a second layer of 150 mg containing 6.84 mg of Ropinirole HCl (equal to 6.00 mg of Ropinirole base) and a third layer of 120.0 mg of granulate barrier. Working as previously described, three-layer tablets are obtained with a mean weight of 400.00 mg, each containing 6.84 mg of Ropinirole HCl, equal to 6.00 mg of base. Table 4 contains the data relating to the release verification of the active principle from the tablets in Example 16.

EXAMPLE 17

Systems Consisting of a Single Three-Layer Tablet—9.00 mg Ropinirole

In Example 17, the first layer consists of 130 mg of a "barrier" layer, the second layer (slow release) contains 10.26 mg of Ropinirole HCl equal to 9.00 mg of base; the third layer consists of 120 mg of a "barrier" layer.

A granulate is prepared as described in Example 13, in section 13(a), the only alteration being to increase the amount of carried active principle, reducing the lactose content by the same amount; such granulate makes up the second layer of the three-layer tablet.

17(a) Preparation of the granulate utilised for the preparation of the slow release layer containing 10.26 mg of Ropinirole HCl equal to 9.00 mg of base.

| Component | Amount (mg) |
|---|---|
| Ropinirole HCl equal to 9.00 mg of base | 10.26 mg |
| Hydroxypropylmethylcellulose (Methocel ® K 100 M, Colorcon, Orpington, UK) | 61.50 mg |
| Sodium carboxymethylcellulose (Blanose 9 M31XF) | 15.00 mg |
| Maltodextrin NF (Lycatab DSH) | 7.50 mg |
| Lactose (C. Erba, Milan, I) | 38.34 mg |
| Hydrogenated castor oil (Cutina HR-Henkel, D) | 15.00 mg |
| Magnesium stearate (C. Erba, Milan, I) | 1.50 mg |
| Colloidal silica (Syloid 244, Grace GmbH, Worms, D) | 0.90 mg |
| Total | 150.00 mg |

For the first and third layer (barrier) a qualitatively and quantitatively identical granulate is employed, as described in Example 13 in section 13(b). The compressing machine is equipped with 8 mm diameter circular concave punches. The machine is set so as to produce three-layer systems consisting of an initial 130.0 mg of granulate barrier, a second layer of 150 mg containing the active principle (equal to 9.00 mg of Ropinirole base) and a third layer of 120.0 mg of granulate barrier. Working as previously described, three-layer tablets are obtained with a mean weight of 400.00 mg, each containing 9.00 mg of active principle. Table 4 contains the data relating to the release verification of the active principle from the tablets in Example 17.

EXAMPLE 18

Systems Consisting of a Single Three-Layer Tablet—12.00 mg Ropinirole

In Example 18, the first layer consists of 130 mg of a "barrier" layer, the second layer (slow release) contains 13.68 mg of Ropinirole HCl equal to 12.00 mg of base; the third layer consists of 120 mg of a "barrier" layer.

A granulate is prepared as described in Example 13, in section 13(a), the only alteration being to increase the amount of carried active principle, reducing the lactose content by the same amount; such granulate makes up the second layer of the three-layer tablet.

18(a) Preparation of the granulate utilised for the preparation of the slow release layer containing 13.68 mg of Ropinirole HCl equal to 12.00 mg of base.

| Component | Amount (mg) |
|---|---|
| Ropinirole HCl equal to 12.00 mg of base | 13.68 mg |
| Hydroxypropylmethylcellulose (Methocel ® K 100 M, Colorcon, Orpington, UK) | 61.50 mg |
| Sodium carboxymethylcellulose (Blanose 9 M31XF) | 15.00 mg |
| Maltodextrin NF (Lycatab DSH) | 7.50 mg |
| Lactose (C. Erba, Milan, I) | 34.92 mg |
| Hydrogenated castor oil (Cutina HR-Henkel, D) | 15.00 mg |
| Magnesium stearate (C. Erba, Milan, I) | 1.50 mg |
| Colloidal silica (Syloid 244, Grace GmbH, Worms, D) | 0.90 mg |
| Total | 150.00 mg |

For the first and third layer (barrier) a qualitatively and quantitatively identical granulate is employed, as described in Example 13 in section 13(b). The compressing machine is equipped with 8 mm diameter circular concave punches. The machine is set so as to produce three-layer systems consisting of an initial 130.0 mg of granulate barrier, a second layer of 150 mg containing the active principle (equal to 12.00 mg of Ropinirole base) and a third layer of 120.0 mg of granulate barrier. Working as described previously, three-layer tablets are obtained with a mean weight of 400.00 mg, each containing 12.00 mg of the active principle. Table 4 contains the data relating to the release verification of the active principle from the tablets in Example 18.

Dissolution Test of Tablets Prepared in Examples 13 to 18

To assess the release characteristics of the active principle from the three-layer tablets, quoted in Examples 13-18, equipment 2 is utilised, paddle (USP XXIII), working at 100 r.p.m. and utilising as dissolution fluid 500 mL of aqueous buffer solution of citrate (pH4.0), at 37° C. The release of the active principle is followed by HPLC assessment at 250 mm utilising an automatic sampling and reading system. The results of the experiments carried out are quoted in Table 4.

TABLE 4

| TIME | Percentage Released in Tablets of Examples 13 to 18 (Ex. 13 to Ex. 18) | | | | | |
|---|---|---|---|---|---|---|
| (hours) | Ex. 13 | Ex. 14 | Ex. 15 | Ex. 16 | Ex. 17 | Ex. 18 |
| 1 | 7.3 | 8.6 | 7.8 | 7.5 | 8.8 | 9.4 |
| 2 | 12.1 | 12.6 | 12.0 | 13.4 | 13.5 | 14.0 |
| 4 | 18.9 | 21.0 | 19.5 | 20.7 | 22.1 | 23.9 |
| 6 | 26.0 | 28.5 | 27.9 | 28.5 | 29.8 | 33.1 |
| 9 | 38.3 | 39.7 | 39.2 | 40.3 | 41.2 | 44.9 |
| 12 | 49.6 | 51.4 | 50.7 | 51.0 | 52.6 | 56.7 |
| 16 | 67.8 | 66.9 | 64.5 | 66.3 | 66.4 | 70.0 |
| 20 | 82.0 | 81.3 | 78.4 | 79.5 | 80.3 | 80.1 |
| 24 | 90.4 | 91.3 | 88.9 | 89.1 | 88.7 | 91.2 |

It is possible to point out that the release of the drug from the prepared systems is slowed down and the release of most of the drug takes approximately 24 hours.

In addition, it is clear that the release kinetics are not substantially modified at any content of active substance in the tablets. Such behaviour is in accordance with the present invention.

EXAMPLE 19

Preparation of Ropinirole Round Tablet Formula

Tablet formulations of ropinirole as a round tablet were prepared as follows. The tablet comprised an upper support or barrier layer (1), an active layer (2) and a lower support or barrier layer (3). HPMC is an abbreviation for hydroxypropylmethylcellulose.

Support Layer (1)

| Component | Role | Amount mg/tablet |
|---|---|---|
| HPMC type 2208/K 100M (100,000 cps) | Hydrophilic matrix polymer | 58.18 |
| Mannitol | Filler, Diluent | 30.68 |
| Glyceryl behenate | Hydrophobic compound | 32.50 |
| Polyvinylpyrolidone (Povidone) | Binder | 6.50 |
| Magnesium stearate | Lubricant | 1.30 |
| Colloidal silicon dioxide | Glidant | 0.52 |
| Yellow ferric oxide | Colouring agent | 0.33 |
| Purified water | Granulation liquid | b |
| Total | | 130.00 |

Active Layer (2)

Described in terms of three tablet strength formulations of ropinirole at 0.75 mg, 1 mg Or 3 mg per tablet ropinirole measured as effective base present.

| | | Amount mg/tablet | | |
|---|---|---|---|---|
| Component | Role | 0.75 mg | 1 mg | 3 mg |
| Ropinirole HCl | Active Substance | 0.855 | 1.14 | 3.42 |
| Lactose monohydrate | Filler, diluent | 47.745 | 47.46 | 45.18 |
| HPMC type 2208/K 100M (100,000 cps) | Hydrophobic matrix polymer | 61.50 (41 wt %) | 61.50 | 61.50 |
| Carboxymethylcellulose sodium | Viscosity regulating agent | 15.00 | 15.00 | 15.00 |
| Maltodextrin | Binder | 7.50 | 7.50 | 7.50 |
| Hydrogenated castor oil | Hydrophobic compound | 15.00 | 15.00 | 15.00 |
| Magnesium stearate | Lubricant | 1.50 | 1.50 | 1.50 |
| olloidal silicon dioxide | Glidant | 0.90 | 0.90 | 0.90 |
| Purified water | Granulation liquid | b | b | b |
| Total | | 150.00 | 150.00 | 150.00 |

Support Layer (3)

| Component | Role | Amount mg/tablet |
|---|---|---|
| HPMC type 2208/K 100M (100,000 cps) | Hydrophilic matrix polymer | 53.70 |
| Mannitol | Filler, Diluent | 28.32 |
| Glyceryl behenate | Hydrophobic compound | 30.00 |
| Polyvinylpyrrolidone (Povidone) | Binder | 6.00 |
| Magnesium stearate | Lubricant | 1.20 |
| Colloidal silicon dioxide | Glidant | 0.48 |
| Yellow ferric oxide | Colouring agent | 0.30 |
| Purified water | Granulation liquid | b |
| Total | | 120.00 |

The purified water included as granulation liquid does not remain in the finished product as indicated by the reference sign "b".

EXAMPLE 20

Preparation of Ropinirole Caplet Formula

Figure 9:
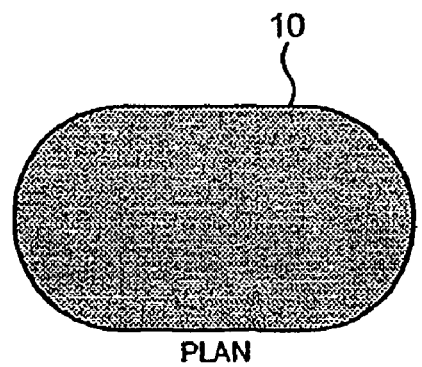
FIG. 9 shows plan, side elevation and end elevation views of a three layer caplet, in which an active substance layer (11), is interposed between barrier layers (10,12); a cross-sectional view is shown through line X-X.
Figure 9:
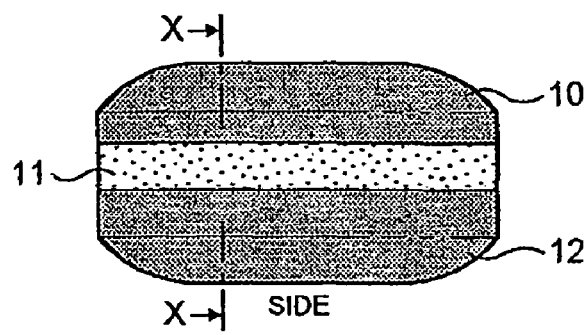
Figure 9:
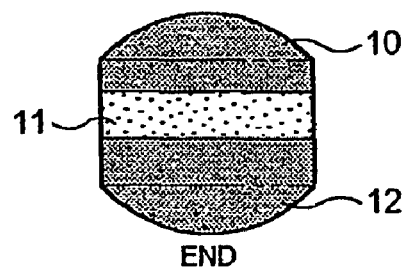
Figure 9:
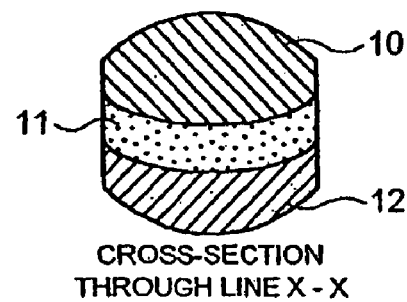

Tablet formulations of ropinirole as a caplet were prepared as follows. The tablet comprised an upper support or barrier layer (1), an active layer (2) and a lower support or barrier layer (3), as shown in FIG. 9 (in which reference numerals 10,12 represent the barrier layers and 1 the active layer). HPMC is an abbreviation for hydroxypropylmethylcellulose. Described in terms of four tablet strength formulations of ropinirole at 1 mg, 3 mg, 6 mg, 9 mg or 12 mg per tablet ropinirole measured as effective base present.

Support Layer (1)

| Component | Role | Amount ropinirole (mg/tablet) | | | |
|---|---|---|---|---|---|
| | | 1 mg | 3 mg | 6 or 9 mg | 12 mg |
| HPMC type 2208 (100,000 cps) | Hydrophilic matrix polymer | 76.07 | 76.07 | 76.07 | 76.07 |
| Mannitol | Filler, diluent | 40.12 | 40.12 | 40.12 | 40.12 |
| Glyceryl behenate | Hydrophobic compound | 42.50 | 42.50 | 42.50 | 42.50 |
| Polyvinylpyrrolidone (Povidone) | Binder | 8.50 | 8.50 | 8.50 | 8.50 |
| Magnesium stearate | Lubricant | 1.70 | 1.70 | 1.70 | 1.70 |
| Colloidal silicon dioxide | Glidant | 0.68 | 0.68 | 0.68 | 0.68 |
| Yellow ferric oxide | Colouring agent | 0.43 | 0.43 | 0.43 | 0.43 |
| Purified water | Granulation liquid | c | c | c | c |
| Total | | 170.00 | 170.00 | 170.00 | 170.00 |

Active Layer (2)

| Component | Role | Amount ropinirole (mg/tablet) | | | | |
|---|---|---|---|---|---|---|
| | | 1 mg | 3 mg | 6 mg | 9 mg | 12 mg |
| Ropinirole HCl | Active substance | 1.14 | 3.42 | 6.84 | 10.26 | 13.68 |
| Lactose monohydrate | Filler, diluent | 47.46 | 45.18 | 41.76 | 38.34 | 34.92 |
| HPMC type 2208 (100,000 cps) | Hydrophilic matrix polymer | 61.50 (41 wt %) | 61.50 | 61.56 | 61.50 | 61.50 |
| Carboxymethyl-cellulose sodium | Viscosity regulating agent | 15.00 | 15.00 | 15.00 | 15.00 | 15.00 |
| Maltodextrin | Binder | 7.50 | 7.50 | 7.50 | 7.50 | 7.50 |
| Hydrogenated castor oil | Hydrophobic compound | 15.00 | 15.00 | 15.00 | 15.00 | 15.00 |
| Magnesium stearate | Lubricant | 1.50 | 1.50 | 1.50 | 1.50 | 1.50 |
| Colloidal silicon dioxide | Glidant | 0.90 | 0.900 | 0.90 | 0.90 | 0.90 |
| Purified water | Granulation liquid | c | c | c | c | c |
| Total | | 150.00 | 150.00 | 150.00 | 150.00 | 150.00 |

Support Layer (3)

|  |  | Amount ropinirole (mg/tablet) | | | |
| --- | --- | --- | --- | --- | --- |
| Component | Role | 1 mg | 3 mg | 6 or 9 mg | 12 mg |
| HPMC type 2208 (100,000 cps) | Hydrophilic matrix polymer | 62.65 | 62.65 | 62.65 | 62.65 |
| Mannitol | Filler, diluent | 33.04 | 33.04 | 33.04 | 33.04 |
| Glyceryl behenate | Hydrophobic compound | 35.00 | 35.00 | 35.00 | 35.00 |
| Polyvinylpyrolidone (Povidone) | Binder | 7.00 | 7.00 | 7.00 | 7.00 |
| Magnesium stearate | Lubricant | 1.40 | 1.40 | 1.40 | 1.40 |
| Colloidal silicon dioxide | Glidant | 0.56 | 0.56 | 0.56 | 0.56 |
| Yellow ferric oxide | Colouring agent | 0.35 | 0.35 | 0.35 | 0.35 |
| Purified water | Granulation liquid | c | c | c | c |
| Total |  | 140.00 | 140.00 | 140.00 | 140.00 |

Film Coating

|  |  | Amount ropinirole (mg/tablet) | | | |
| --- | --- | --- | --- | --- | --- |
| Component | Role | 1 mg | 3 mg | 6 or 9 mg | 12 mg |
| OPADRY OY-S-28876 WHITE | Coating agent | 13.80 | 13.80 | 13.80 | 13.80 |
| Purified water | Coating liquid | c | c | c | c |
| Total tablet weight (layers 1, 2, 3 and coat) |  | 473.80 | 473.80 | 473.80 | 473.80 |

The purified water included as granulation liquid or coating liquid does not remain in the finished product as indicated by the reference sign "c". OPADRY OY-S-28876 WHITE is 63% HPMC 2910 6 cP, 7% PEG 400, 30% TiO2. Red/pink (0.01-0.25%) and/or yellow (0.1 to 1.5%) colourings can also be added (iron oxides), the HPMC varying between 61-66%. An alternative blue coating uses 31-32% each of HPMC 2910 3 cP and HPMC 2910 5 cP, 8% PEG400, 23-24% TiO2, 1% polysorbate, and indigotine as blue dye at 4-5%.

EXAMPLE 21

Preparation of Ropinirole Caplet Formula

Tablet formulations of ropinirole as a caplet were prepared as follows. The tablet comprised an upper support or barrier layer (1), an active layer (2) and a lower support or barrier layer (3), as with example 20. Described in terms of four tablet strength formulations of ropinirole at 1 mg, 3 mg, 6 mg, 9 mg and 12 mg per tablet ropinirole measured as effective base present. This example is the same as Example 20 but the yellow ferric oxide in the support or barrier layers are absent.

Support Layer (1)

| Component | Role | Amount ropinirole (mg/tablet) 1, 3 or 6 mg |
| --- | --- | --- |
| HPMC type 2208 (100,000 cps) | Hydrophilic matrix polymer | 76.50 |
| Mannitol | Filler, diluent | 40.12 |
| Glyceryl behenate | Hydrophobic compound | 42.50 |
| Polyvinylpyrolidone (Povidone) | Binder | 8.50 |
| Magnesium stearate | Lubricant | 1.70 |
| Colloidal silicon dioxide | Glidant | 0.68 |
| Purified water | Granulation liquid | d |
| Total |  | 170.00 |

Active Layer (2)

|  |  | Amount ropinirole (mg/tablet) | | | | |
| --- | --- | --- | --- | --- | --- | --- |
| Component | Role | 1 mg | 3 mg | 6 mg | 9 mg | 12 mg |
| Ropinirole HCl | Active substance | 1.14 | 3.42 | 6.84 | 10.26 | 13.68 |
| Lactose monohydrate | Filler, diluent | 47.46 | 45.18 | 41.76 | 38.34 | 34.92 |
| HPMC type 2208 (100,000 cps) | Hydrophilic matrix polymer | 61.50 (41 wt %) | 61.50 | 61.50 | 61.50 | 61.50 |
| Carboxymethyl-cellulose sodium | Viscosity regulating agent | 15.00 | 15.00 | 15.00 | 15.00 | 15.00 |
| Maltodextrin | Binder | 7.50 | 7.50 | 7.50 | 7.50 | 7.50 |
| Hydrogenated castor oil | Hydrophobic compound | 15.00 | 15.00 | 15.00 | 15.00 | 15.00 |
| Magnesium stearate | Lubricant | 1.50 | 1.50 | 1.50 | 1.50 | 1.50 |
| Colloidal silicon dioxide | Glidant | 0.90 | 0.900 | 0.90 | 0.90 | 0.90 |
| Purified water | Granulation liquid | c | c | c | c | c |
| Total |  | 150.00 | 150.00 | 150.00 | 150.00 | 150.00 |

Support Layer (3)

| Component | Role | Amount ropinirole (mg/tablet) 1, 3 or 6 mg |
| --- | --- | --- |
| HPMC type 2208 (100,000 cps) | Hydrophilic matrix polymer | 63.00 |
| Mannitol | Filler, diluent | 33.04 |

-continued

| Component | Role | Amount ropinirole (mg/tablet) 1, 3 or 6 mg |
|---|---|---|
| Glyceryl behenate | Hydrophobic compound | 35.00 |
| Polyvinylpyrolidone (Povidone) | Binder | 7.00 |
| Magnesium stearate | Lubricant | 1.40 |
| Colloidal silicon dioxide | Glidant | 0.56 |
| Purified water | Granulation liquid | d |
| Total | | 140.00 |

Film Coating

| | | Amount ropinirole (mg/tablet) | | | |
|---|---|---|---|---|---|
| Component | Role | 1 mg | 3 mg | 6 or 9 mg | 12 mg |
| OPADRY OY-S-28876 WHITE | Coating agent | 13.80 | 13.80 | 13.80 | 13.80 |
| Purified water | Coating liquid | d | d | d | d |
| Total tablet weight (layers 1, 2, 3 and coat) | | 473.80 | 473.80 | 473.80 | 473.80 |

The purified water included as granulation liquid or coating liquid does not remain in the finished product as indicated by the reference sign "d".

EXAMPLES 22 AND 23

Preparation of Ropinirole Caplet Formula

Tablet formulations of ropinirole as a caplet were prepared as follows. The tablet comprised an upper support or barrier layer (1), an active layer (2) and a lower support or barrier layer (3), as for Examples 20 and 21. Example formulations 22 and 23 are described as a single tablet strength formulation each of ropinirole at 0.75 mg per tablet ropinirole measured as effective base present (0.855 mg measured as the HCl salt). As can be seen, Examples 22 and 23 involve identical active layers to the 0.75 mg ropinirole active layer of Example 19, but different barrier layers to Example 19, with different amounts and grades of HPMC in the barrier layers, replacement of mannitol with lactose, and lower amounts of glyceryl behenate. As can be seen, Examples 22 and 23 have 10% and 40 weight % respectively of K4M HPMC in their barrier layers which gives a slightly faster release profile in vitro than the ca. 45 wt % K100M HPMC present in the barrier layers of Examples 13-18 and 19-21, as inter alia the ropinirole migrates faster through the barrier layers. Example 22 has 20 wt % of K100LV HPMC as well as 10 wt % K4M HPMC in the barrier layer—the low-viscosity (LV) HPMC in the barrier layer may increase water uptake and aid gelling, increasing the matrix viscosity and decreasing the release rate.

Support Layer (1) for Examples 22, 23

| | | Amount (mg/tablet) | |
|---|---|---|---|
| Component | Role | Example 22 | Example 23 |
| HPMC K 4M | Hydrophilic matrix polymer | 13.00 | 51.84 |

-continued

| | | Amount (mg/tablet) | |
|---|---|---|---|
| Component | Role | Example 22 | Example 23 |
| HPMC K100LV | Hydrophilic matrix polymer | 26.00 | |
| Lactose monohydrate | | 64.68 | 51.84 |
| Glyceryl behenate | Hydrophobic compound | 17.56 | 17.55 |
| Polyvinylpyrolidone (Povidone) | Binder | 6.50 | 6.50 |
| Magnesium stearate | Lubricant | 1.30 | 1.30 |
| Colloidal silicon dioxide | Glidant | 0.64 | 0.63 |
| Yellow ferric oxide | Colouring agent | 0.32 | 0.32 |
| Purified water | Granulation liquid | c | c |
| Total | | 130.00 | 130.00 |

Active Layer (2) for Examples 22 and 23

Described in terms of three tablet strength formulations of ropinirole at 0.75 mg per tablet ropinirole measured as effective base present.

| Component | Role | Amount ropinirole mg/tablet 0.75 mg |
|---|---|---|
| Ropinirole HCl | Active Substance | 0.855 |
| Lactose monohydrate | Filler, diluent | 47.745 |
| HPMC type 2208/K 100M (100,000 cps) | Hydrophobic matrix polymer | 61.50 |
| Carboxymethylcellulose sodium | Viscosity regulating agent | 15.00 |
| Maltodextrin | Binder | 7.50 |
| Hydrogenated castor oil | Hydrophobic compound | 15.00 |
| Magnesium stearate | Lubricant | 1.50 |
| Colloidal silicon dioxide | Glidant | 0.90 |
| Purified water | Granulation liquid | c |
| Total | | 150.00 |

Support Layer (3) for Examples 22, 23

| | | Amount (mg/tablet) | |
|---|---|---|---|
| Component | Role | Example 22 | Example 23 |
| HPMC K4M | Hydrophilic matrix polymer | 12.00 | 47.86 |
| HPMC K100LV | | 24.00 | |
| Lactose monohydrate | | 59.70 | 47.86 |
| Glyceryl behenate | Hydrophobic compound | 16.20 | 16.20 |
| Polyvinylpyrolidone (Povidone) | Binder | 6.00 | 6.00 |
| Magnesium stearate | Lubricant | 1.20 | 1.20 |
| Colloidal silicon dioxide | Glidant | 0.60 | 0.60 |
| Yellow ferric oxide | Colouring agent | 0.30 | 0.30 |
| Purified water | Granulation liquid | c | c |
| Total | | 120.00 | 120.00 |

The purified water included as granulation liquid or coating liquid does not remain in the finished product as indicated by the reference sign "c".

Note: The active layer for each Example 22 and 23 above can be replaced by the active layers of examples 20 and 21 using 1 mg, 3 mg, 6 mg, 9 mg and 12 mg ropinirole measured as effective base present.

Note: in all the ropinirole examples 13-18 and 19-23, higher doses of up to 24 mg ropinirole per day can be administered by e.g. 2×12 mg tablets. Other doses e.g. 4 mg per day can be administered using 1×1 mg and 1×3 mg tablet per day. Also, in any of the Examples 13-23, different doses of for example 0.25 mg, 0.5 mg and 2 mg ropinirole can be used in the active layer by varying the amount of lactose while keeping the total weight of the active layer constant.

EXAMPLE 24

Further Studies on Caplet Preparation and Drug Dissolution Profiles

The following further studies on caplet preparation are presented to show drug dissolution profiles for ropinirole caplets containing 0.75 mg, 6 mg or 12 mg ropinirole measured as effective base present.

| Formulation of Ropinirole HCl CR caplet, detailed per layer, mg/tablet | | | |
|---|---|---|---|
| Ingredients | | | |
| Layer 1, support layer D14-4 Yellow | | | |
| HPMC type 2208 (100 000 cps) | | 76.075 | |
| Mannitol | | 40.120 | |
| Glyceryl behenate | | 42.500 | |
| Povidone | | 8.500 | |
| Yellow ferric oxide | | 0.425 | |
| Magnesium stearate vegetable | | 1.700 | |
| Colloidal silicon dioxide | | 0.680 | |
| Purified water | | a | |
| Total | | 170.000 | |
| Layer 2, active layer | 0.75 mg | 6 mg | 12 mg |
| Ropinirole HCl | 0.855 | 6.840 | 13.680 |
| Lactose monohydrate | 47.745 | 41.760 | 34.920 |
| HPMC type 2208 (100 000 cps) | 61.500 | 61.500 | 61.500 |
| Carboxymethlycellulose sodium | 15.000 | 15.000 | 15.000 |
| Maltodextrin | 7.500 | 7.500 | 7.500 |
| Hydrogenated castor oil | 15.000 | 15.000 | 15.000 |
| Magnesium stearate vegetable | 1.500 | 1.500 | 1.500 |
| Colloidal silicon dioxide | 0.900 | 0.900 | 0.900 |
| Purified water | a | a | a |
| Total, layer 2 | 150.000 | 150.000 | 150.000 |
| Layer 3, support layer D14-4 Yellow | | | |
| HPMC type 2208 (100 000 cps) | | 62.650 | |
| Mannitol | | 33.040 | |
| Glyceryl behenate | | 35.000 | |
| Povidone | | 7.000 | |
| Yellow ferric oxide | | 0.350 | |
| Magnesium stearate vegetable | | 1.400 | |
| Colloidal silicon dioxide | | 0.560 | |
| Purified water | | a | |
| Total | | 140.000 | |
| Film coating | | | |
| OPADRY OY-S-28876 WHITE | | 13.800 | |
| Purified water | | a | |
| Total, tablet | | 473.800 | |

Notes:
a = Does not remain in the final product 0.855 mg of Ropinirole HCl is corresponding to 0.75 mg of Ropinirole Base 6.840 mg of Ropinirole HCl is corresponding to 6.00 mg of Ropinirole Base 13.680 mg of Ropinirole HCl is corresponding to 12.00 mg of Ropinirole Base The drug release profiles were measured using standard techniques. The results were as follows (results presented in terms of percentage drug released at given time intervals in hours):

| Analytical results | | | | | | | | | |
|---|---|---|---|---|---|---|---|---|---|
| Dosage, mg | 0.75 | 0.75 | 0.75 | 6 | 6 | 6 | 12 | 12 | 12 |
| Batch no. | C511 | C519 | C529 | C530 | C531 | C532 | C512 | C534 | C535 |
| Tablet | P00K41E | P00K40E | P00K39E | P00K45E | P00K46E | P00K47E | P00K42E | P00K43E | P00K44E |
| Tablet weight, mg | 471.95 | 472.32 | 472.08 | 474.08 | 471.50 | 473.37 | 470.39 | 473.62 | 474.78 |
| Tablet wt RSD, % | 0.78 | 1.44 | 0.65 | 0.98 | 1.10 | 1.08 | 0.93 | 1.28 | 1.02 |
| Time, h | | | | | | | | | |
| 0.00 | 0.00 | 0.00 | 0.00 | 0.00 | 0.00 | 0.00 | 0.00 | 0.00 | 0.00 |
| 1.00 | 8.96 | 6.88 | 7.43 | 8.67 | 8.20 | 8.71 | 9.45 | 10.10 | 9.73 |
| 2.00 | 12.42 | 11.45 | 11.69 | 13.47 | 13.17 | 13.48 | 14.87 | 15.53 | 15.23 |
| 4.00 | 19.99 | 19.93 | 19.59 | 22.03 | 22.01 | 21.55 | 24.37 | 24.87 | 24.55 |
| 6.00 | 27.45 | 27.62 | 27.43 | 30.21 | 29.65 | 30.17 | 33.38 | 33.74 | 33.33 |
| 9.00 | 38.24 | 38.60 | 38.34 | 41.68 | 41.46 | 41.81 | 45.56 | 46.22 | 45.81 |
| 12.00 | 49.78 | 49.58 | 50.00 | 52.07 | 52.36 | 52.33 | 56.81 | 57.40 | 56.71 |
| 16.00 | 64.53 | 64.48 | 65.47 | 66.17 | 66.41 | 66.26 | 69.54 | 70.90 | 69.52 |
| 20.00 | 77.17 | 76.98 | 78.68 | 78.01 | 78.34 | 78.72 | 80.95 | 81.64 | 79.95 |
| 24.00 | 85.79 | 86.17 | 88.18 | 87.09 | 87.69 | 88.19 | 89.07 | 89.76 | 88.12 |
| 30.00 | 92.40 | 93.57 | 95.40 | 95.26 | 94.81 | 95.41 | 95.76 | 96.63 | 94.60 |
| 36.00 | 94.37 | 96.00 | 97.19 | 97.96 | 97.17 | 97.58 | 97.80 | 99.38 | 97.26 |

We claim:
1. A multi-layer controlled release tablet, consisting of:
(a) one active layer which consists of:
   (i) 0.05-20% by weight of ropinirole, inclusive of pharmaceutically acceptable salts thereof,
   (ii) hydrophilic polymeric substances which swell and gel and/or erode upon contact with aqueous liquids,
   (iii) lipophilic substances, and
   (iv) 5-50% by weight of adjuvant substances,
   wherein the weight ratio of the hydrophilic polymeric substances to the lipophilic substances contained in said active layer is in the range of 7:1 to 1:1, and in which said hydrophilic polymeric substances (ii) are contained in a percentage between 30% and 75% of the weight of the active layer, and
(b) one or more barrier layers which limit the release surface of the active layer, which barrier layers contain one or more of: hydrophilic polymeric substances which swell and/or gel and/or erode upon contact with aqueous liquids, lipophilic substances and adjuvant substances; which tablet is optionally coated.

2. The multi-layer controlled release tablet of claim 1, wherein the active substance is ropinirole hydrochloride.

3. The multi-layer controlled release tablet of claim 1, in which said lipophilic substances (iii) are contained in a percentage between 5% and 55% of the weight of the active layer.

4. The multi-layer controlled release tablet of claim 1, in which said adjuvant substances (iv) are contained in a percentage between 10% to 40% of the weight of the active layer.

5. The multi-layer controlled release tablet of claim 1, in which said hydrophilic polymeric substances comprise a pharmaceutically acceptable biocompatible and/or biodegradable material, selected from the group consisting of non-cross-linked polyvinylpyrrolidone, hydroxypropylcellulose with a molecular weight of 100,000 to 4,000,000, sodium carboxymethylcellulose, potassium methacrylate-divinylbenzene copolymer, hydroxypropylmethylcellulose of molecular weight between 2,000 and 4,000,000, a polyethyleneglycol of molecular weight between 200 and 15,000, a polyoxyethylene with molecular weight of up to 20,000,000, a carboxyvinylpolymer, a poloxamer (polyoxyethylene-polyoxypropylene copolymer) a polyvinylalcohol, a glucane (glucan), a carrageenan, a scleroglucane (scleroglucan), a mannan, a galactomannan, gellans, xanthans, alginic acid, polyaminoacids, methyl vinyl ether/maleic anhydride copolymer, carboxymethylcellulose, ethylcellulose, methylcellulose, starch, and alpha, beta or gamma cyclodextrin.

6. The multi-layer controlled release tablet of claim 1, wherein the hydrophilic polymeric substances in the active layer comprise:
(a) one or more of the following: hydroxypropylcellulose with a molecular weight between 100,000 and 4,000,000, hydroxypropylmethylcellulose (HPMC) with a molecular weight between 2,000 and 4,000,000, ethylcellulose or methylcellulose; and
b) sodium carboxymethylcellulose, carboxymethylcellulose, hydroxypropylcellulose with a molecular weight of from 100,000 to 4,000,000, a carboxyvinyl polymer, a carrageenan, a xanthan, alginic acid, ethylcellulose, methylcellulose, dextrin and/or maltodextrin.

7. The multi-layer controlled release tablet of claim 6, wherein the hydrophilic polymeric substances in the active layer include hydroxypropylmethylcellulose and sodium carboxymethylcellulose.

8. The multi-layer controlled release tablet of claim 5, wherein the hydrophilic polymeric substances in the active layer comprise hydroxypropylmethylcellulose having a molecular weight in the range 20,000 and 500,000 or a 2% viscosity in the range of 80,000 to 120,000 mPa.sec.

9. The multi-layer controlled release tablet of claim 8, wherein the hydrophilic polymeric substances in the active layer comprise hydroxypropylmethylcellulose having a molecular weight of about 250,000.

10. The multi-layer controlled release tablet of claim 5, wherein the hydroxypropylmethylcellulose in the active layer is a gellable hydroxypropylmethylcellulose.

11. The multi-layer controlled release tablet of claim 1, in which said lipophilic substances include a natural fat as such or totally or partially hydrogenated, beeswax, polyethyoxylated beeswax, a mono-, bi-, or tri-substituted glyceride, glyceryl palmitostearate, glyceryl behenate, diethyleneglycol palmitostearate, a polyethyleneglycol stearate, a polyoxyethyleneglycol palmitostearate, glyceryl monopalmitostearate, cetyl palmitate, polyethyleneglycol palmitostearate, mono- or di-glyceryl behenate, cetyl alcohol, stearic acid, a saturated or unsaturated fatty acid, and/or hydrogenated castor oil.

12. The multi-layer controlled release tablet of claim 11, in which the lipophilic substance present in the active layer is selected from hydrogenated castor oil and glyceryl behenate.

13. The multi-layer controlled release tablet of claim 1, in which the active substance is ropinirole inclusive of pharmaceutically acceptable salts thereof contained in a percentage of 0.05% to 20% by weight of the active layer, (ii) the hydrophilic polymeric substance comprises hydroxypropylmethylcellulose, sodium carboxymethylcellulose or calcium carboxymethylcellulose, (iii) the lipophilic substance comprises hydrogenated castor oil or glyceryl behenate, and (iv) the adjuvant substances are contained in a percentage of 5% to 50% by weight of the active layer, and the weight ratio of the hydrophilic polymeric substances to the lipophilic substances contained in the active layer is in the range of from 7:1 to 1:1.

14. The multi-layer controlled release tablet of claim 1, in which the weight ratio of hydrophilic swelling and/or gelling and/or erodable polymeric substances to lipophilic substances contained in the barrier layer is in the range of 1:1 to 7.5:1.

15. The multi-layer controlled release tablet of claim 1, in which the amount of ropinirole present, inclusive of pharmaceutically acceptable salts thereof, is up to 12.0 mg, measured as the amount of ropinirole base present.

16. The multi-layer controlled release tablet of claim 15, in which the amount of ropinirole present, inclusive of pharmaceutically acceptable salts thereof, is from 0.75 mg to 12 mg, measured as the amount of ropinirole base present.

17. The multi-layer controlled release tablet of claim 1, in which said one or more barrier layers are applied to one or both surfaces (bases) of the active layer.

18. The multi-layer controlled release tablet of claim 17, wherein a barrier layer is applied to both surfaces (bases) of the active layer 19. The multi-layer controlled release tablet of claim 1, wherein release of ropinirole during the first hour after oral administration or immersion in aqueous liquids occurs only from the surface of the tablet not covered by the one or more barrier layers.

20. The multi-layer controlled release tablet of claim 1, which consists of an active layer and two barrier layers, one barrier layer being applied to each surface (base) of the active layer, wherein the active layer weighs about 150 mg and consists essentially of up to 12 mg ropinirole HCl (measured as the amount of ropinirole base present), 41% HPMC type 2208 (100,000 cps), 10% carboxylmethylcellulose sodium, 5% maltodextrin, 10% hydrogenated castor oil, 1% magnesium stearate, 0.6% colloidal silicon dioxide and lactose monohydrate quantum sufficiat, and wherein the barrier layers weigh between 120-170 mg, the barrier layers consisting essentially of 23.6% mannitol, 25% glyceryl behenate, 5% polyvinylpyrrolidone, 1% magnesium stearate, 0.4% colloidal silicon dioxide, HPMC type 2208 (100,000 cps) and optionally a colouring agent ana quantum sufficiat, wherein said controlled release tablet is optionally film coated with about 13.80 mg of a coating agent.

21. The multi-layer controlled release tablet of claim 20, wherein the active layer weighs 150 mg and consists of up to 12 mg ropinirole HCl (measured as the amount of ropinirole base present), 41% HPMC type 2208 (100,000 cps), 10% carboxylmethylcellulose sodium, 5% maltodextrin, 10% hydrogenated castor oil, 1% magnesium stearate, 0.6% colloidal silicon dioxide and lactose monohydrate quantum sufficiat, and wherein the barrier layers weigh between 120-170 mg, the barrier layers consisting of 23.6% mannitol, 25% glyceryl behenate, 5% polyvinylpyrrolidone, 1% magnesium stearate, 0.4% colloidal silicon dioxide, HPMC type 2208 (100,000 cps) and optionally a colouring agent ana quantum sufficiat, wherein said controlled release tablet is optionally film coated with 13.80 mg of a coating agent.

22. The multi-layer controlled release tablet of claim 21, wherein one barrier layer weighs about 170 mg and the other barrier layer weighs about 140 mg.

23. The multi-layer controlled release tablet of claim 22, wherein one barrier layer weighs 170 mg and the other barrier layer weighs 140 mg.

24. The multi-layer controlled release tablet of claim 23, wherein said tablet is film coated with 13.80 mg of a coating agent.

25. The multi-layer controlled release tablet of claim 21, wherein one barrier layer weighs about 130 mg and the other barrier layer weighs about 120 mg.

26. The multi-layer controlled release tablet of claim 25, wherein one barrier layer weighs 130 mg and the other barrier layer weighs 120 mg.

27. The multi-layer controlled release tablet of claim 26, wherein said tablet is uncoated.

28. The multi-layer controlled release tablet of claim 21, wherein said barrier layers contain a colouring agent.

29. The multi-layer controlled release tablet of claim 28, wherein said colouring agent is yellow ferric oxide.

30. The multi-layer controlled release tablet of claim 21, wherein the amount of ropinirole HCl in the active layer is 0.75-12 mg, measured as the amount of ropinirole free base present.

31. The multi-layer controlled release tablet of claim 1, which tablet is not coated by a film of gastroresistant and enterosoluble polymeric material.

32. The multi-layer controlled release tablet of claim 1, in which the tablet preparation is carried out by compression of the powder or granular mixture and working between 1000 and 5000 Kg/cm$^2$.

33. A method of treating Parkinson's Disease comprising administering to a human in need of such treatment one or more multi-layer controlled release tablets as defined in any preceding claim.

34. The method of claim 33, in which one or more multi-layer controlled release tablets are administered once per day to the human in need of such treatment.

35. The method The claim 34, in which a single multi-layer controlled release tablet is administered once per day to the human in need of such treatment.

* * * * *